(12) United States Patent
Schneider et al.

(10) Patent No.: US 9,221,863 B2
(45) Date of Patent: Dec. 29, 2015

(54) TRANSIENTLY BONDING DRAG-TAGS FOR SEPARATION MODALITIES

(75) Inventors: James W. Schneider, Pittsburgh, PA (US); Shane T. Grosser, Princeton, NJ (US); Jeffrey M. Savard, McGaheysville, VA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 957 days.

(21) Appl. No.: 12/665,994

(22) PCT Filed: Jun. 23, 2008

(86) PCT No.: PCT/US2008/067856
§ 371 (c)(1),
(2), (4) Date: Mar. 3, 2010

(87) PCT Pub. No.: WO2009/020710
PCT Pub. Date: Feb. 12, 2009

(65) Prior Publication Data
US 2010/0213059 A1    Aug. 26, 2010

Related U.S. Application Data

(60) Provisional application No. 60/936,728, filed on Jun. 22, 2007.

(51) Int. Cl.
*G01N 27/26* (2006.01)
*C07H 21/00* (2006.01)
(Continued)

(52) U.S. Cl.
CPC .......... *C07H 19/04* (2013.01); *G01N 2030/582* (2013.01)

(58) Field of Classification Search
CPC ............................................... G01N 2030/582

USPC .......................................... 204/450; 536/23.1
See application file for complete search history.

(56) References Cited

U.S. PATENT DOCUMENTS

| 5,190,761 | A | 3/1993 | Liburdy |
| 6,450,632 | B1 | 9/2002 | Tsang et al. |
| 2006/0177840 | A1 | 8/2006 | Slater et al. |

FOREIGN PATENT DOCUMENTS

| CA | 2 523 089 | * | 5/2006 | ............. C07H 11/06 |

OTHER PUBLICATIONS

Grosser et al., "Sequence Specific Separation of Target DNA in Micellar Electrokinetic Chromatography" Abstract Submitted to: TA008—New Developments in Bioanalytical CE and Microdevice Technology, Presented Wednesday, Nov. 2, 2005.*

(Continued)

*Primary Examiner* — Luan Van
*Assistant Examiner* — Steven Rosenwald
(74) *Attorney, Agent, or Firm* — The Webb Law Firm

(57) ABSTRACT

The invention relates transiently attaching drag-tags to molecules during electrophoresis. The invention includes running buffers having drag-tags that transiently attach to lipophilic moieties attached to the molecules. The lipophilic moieties can be covalently or ionically bonded to the molecules. One particular aspect of the invention is a nucleoside analog or a nucleic acid analog comprising a lipophilic moiety. The invention is also directed to methods of separating molecules that comprise a lipophilic moiety. The methods generally comprise transiently attaching a drag-tag to the lipophilic moiety during a separation modality. These methods can be used to separate the molecules by size or weight, to measure a hydrodynamic radius of a drag-tag, or to separate a plurality of drag-tag by their hydrodynamic radius.

18 Claims, 16 Drawing Sheets

(51) Int. Cl.
 C07K 1/00 (2006.01)
 C07H 19/04 (2006.01)
 G01N 30/58 (2006.01)

(56) References Cited

OTHER PUBLICATIONS

Schneider, Front-End Processing of Cell Lysates for Enhanced Chip-Based Detection, Accession No. ADA456327, published Jul. 28, 2006.*
Won et al., Electrophoresis 2005, 26, 2138-2148.*
Hyrup and Neilsen (Bioorganic & Medicinal Chemistry, vol. 4, No. 1, pp. 5-23, 1996).*
Haynes, et al. (Bioconjugate Chem. 2005, 16, 929-938).*
Godovikova et al., Active derivatives of oligonucleotides with a zwitterionic terminal phosphate group for design of affinity reagents and probes, Bioorganicheskaia khimiia, (1989), vol. 15, No. 9, pp. 1246-1252. (Abstract Only).
Stellwagen et al., Electrokinetic mobility of short DNA oligomers, American Chemical Society, (2003) (Abstract Only).
Sanger et al., DNA sequencing with Chain-Terminating Inhibitors, Proc. Natl. Acad. Sci. USA, (Dec. 1977), vol. 74, No. 12, pp. 5463-5467.
Sanger et al., A Rapid Method for Determining Sequences in DNA by Primed Synthesis with DNA Polmerase, J. Mol. Biol. (1975), vol. 94, pp. 441-448.
Rosenblum et al., New Dye-Labeled Terminators for Improved DNA Sequencing Patterns, Nucleic Acids Research, 1997, vol. 25, No. 22, pp. 4500-4504.
Lee et al., New Energy Transfer Dyes for DNA Sequencingt, Nucleic Acids Research, (1997), vol. 25, No. 14, pp. 2816-2822.
Slater et al., On the Stretching of DNA in the Reptation Theories of Gel Electrophoresis, Biopolymers, (1987), vol. 26, pp. 863-872.
Slater et al., The Biased Reptation Model of DNA Gel Electrophoresis: Mobility vs. Molecular Size and Gel Concentration, Biopolymers, (1989), vol. 28, pp. 1781-1791.
Noolandi et al., Generalized Tube Model of Biased Reptation for Gel Electrophoresis of DNA, Science, (Mar. 17, 1989), vol. 243, pp. 1456-1458.
Viovy, Electrophoresis of DNA and Other Polyelectrolytes: Physical Mechanisms, Review of Modern Physics, (Jul. 2000), vol. 72, No. 3, pp. 813-872.
Barron et al., Capillary Electrophoresis of DNA in Uncrosslinked Polymer Solutions: Evidence for a New Mechanism of DNA Separation, Biotechnology and Bioengineering, (1996), vol. 52, pp. 259-270.
Albarghouthi et al., Polymeric Matrices for DNA Sequencing by Capillary Electrophoresis, Electrophoresis, (2000), vol. 21, pp. 4096-4111.
Albarghouthi et al., Poly-N-Hydroxyethylacrylamide (polyDuramide): A Novel, Hydrophilic, Self-coating Polymer Matrix for DNA Sequencing by Capillary Electrophoresis, Electrophoresis, (2002), vol. 23, pp. 1429-1440.
Heller et al., Separation of Double-Stranded and Single-Stranded DNA in Polymer Solutions: I. Mobility and Separation Mechanism, Electrophoresis, (1999), vol. 20, pp. 1962-1977.
Heller et al., Separation of Double-Stranded and Single-Stranded DNA in Polymer Solutions: II. Separation, Peak Width and Resolution, Electrophoresis, (1999), vol. 20, pp. 1978-1986.
Ronaghi, Pyrosequencing Sheds Light on DNA Sequencing, Genome Research, (2001) pp. 3-11.
Ronaghi et al., A Sequencing Method Based on Real-Time Pyrophosphate, Science, (Jul. 17, 1998), vol. 281, No. 5375, pp. 363-365.
Mashayekhi et al., Analysis of Read Length Limiting Factors in Pyrosequencing Chemistry, Analytical Biochemistry, (2007), vol. 363, pp. 275-287.
Franca et al., A Review of DNA Sequencing Techniques, Quarterly Reviews of Biophysics, (2002), vol. 35, pp. 169-200.
Ronaghi et al., Real-Time DNA Sequencing Using Detection of Pyrophosphate Release, Analytical Biochemistry, (1996), vol. 242, pp. 84-89.
Margulies et al., Genome Sequencing in Microfabricated High-Density Picolitre Reactors, Nature, (Sep. 2005), vol. 437, pp. 376-380.
Leamon et al., A Massively Parallel PicoTiterPlate Based Platform for Discrete Picoliter-Scale Polymerase Chain Reactions, Electrophoresis, (2003), vol. 24, pp. 3769-3777.
Brenner et al., Gene Expression Analysis by Massively Parallel Signature Sequencing (MPSS) on Microbead Arrays, Nature Biotechnology, (Jun. 2000), vol. 18, pp. 630-634.
Beard, Efficiency of Correct Necleotide Insertion Governs DNA Polymerase Fidelity, The Journal of Biological Chemistry, (Oct. 4, 2002), vol. 277, No. 49, pp. 47393-47398.
Metzker et al., Termination of DNA Synthesis by Novel 3'-modified-deoxyribonucleoside 5"-triphosphates, Nucleic Acids Research, (1994), vol. 22, No. 20, pp. 4259-4267.
Meagher et al., End-Labeled Free-Solution Electrophoresis of DNA, Electrophoresis, (2005), vol. 26, pp. 331-350.
Long et al., Electrophoresis of Polyampholytes, A Journal of Chemical Physics, (Jan. 15, 1998), vol. 108, pp. 1234-1244.
Lu et al., DNA Persistence Length Revisted, Biopolymers, (2002), vol. 61, pp. 261-275.
Mohanty et al., Free Solution Mobility of Oligomeric DNA, Biopolymers, (1999), vol. 49, pp. 209-214.
Stellwagen et al., The Free Solution Mobility of DNA in Tris-acetate-EDTA buffers of Different Concentrations, with and without added NaCl, Electrophoresis, (2002), vol. 23, pp. 1935-1941.
Heller et al., Free-Solution Electrophoresis of DNA, Journal of Chromatography, (1998), vol. 806, pp. 113-121.
Ren et al., Separating DNA Sequencing Fragments Without a Sieving Matrix, Electrophoresis, (1999), vol. 20, pp. 2501-2509.
Slater et al., Theory of DNA Electrophoresis: A look at some current challenges, Electrophoresis, (2000), vol. 21, pp. 3873-3887.
Meagher et al., Free-Solution Electrophoresis of DNA Modified with Drag-Tags at Both Ends, Electrophoresis, (2000), vol. 27, pp. 1702-1712.
Terabe et al., Electrokinetic Separations with Micellar Solutions and Open-Tubular Capillaries, Analytical Chemistry (1984), vol. 56, pp. 111-113.
Terabe et al., Electrokinetic Chromatography with Micellar Solution and Open-Tubular Capillary, Anal. Chem., (1985), vol. 57, pp. 834-841.
Guarnieri et al., Micellar Electrokinetic Capillary Chromatography of 8-hydroxydeoxyguanosine and other oxidized derivatives of DNA, Journal of Chromatography, (1994), vol. 656, pp. 209-213.
Wirtz et al., Determination of the DNA Methylation Level in Tumor Cells by Capillary Electrophoresis and Laser-Induced Fluorescence Detection, Electrophoresis, (2004), vol. 25, pp. 839-845.
Wirtz et al., Capillary Electrophoresis-laser-induced Fluorescence Analysis of Endogenous Damage in Mitochondrial and Genomic DNA, Electrophoresis, (2005), vol. 26, pp. 2599-2607.
Molina et al., Simultaneous Determination of Phosphorus-containing Amino Acid-Herbicides by Nonionic Surfactant Micellar Electrokinetic Chromatography with laser-induced Fluorescence Detection, Electrophoresis, (2001), vol. 22, pp. 1175-1181.
Molina et al., Analytical Potential of Fluorescein Analogues for Ultrasensitive Determinations of Phosphorus-containing amino Acid Herbicides by Micellar Electrokinetic Chromatography with laser-induced Fluorescence Detection, Electrophoresis, (2002), vol. 23, pp. 1096-1103.
Croubels et al., Capillary Electrophoresis of Some Tetracycline Antibiotics, Journal of Chromatography, (1994), vol. 673, pp. 267-274.
Grimm et al., Effect of Different Surfactants on the Separation by Micellar Electrokinetic Chromatography of a Complex Mixture of Dipeptides in Urine of Prolidase-deficient Patients, Journal of Chromatography, (1997), vol. 698, pp. 47-57.
Swedberg, Use of non-ionic and zwitterionic surfactants to enhance selectivity in high-performance capillary electrophoresis, Journal of Chromatography, (1990), vol. 503, pp. 449-452.
Le et al., Electrophoretic separations of twelve phenothiazines and N-demethyl derivatives by using capillary zone electrophoresis and

(56) References Cited

OTHER PUBLICATIONS micellar electrokinetic chromatography with non ionic surfactant, Journal of Chromatography, (2005), vol. 1063, pp. 235-240.

Lupi et al., Separation of closely related peptide substrates of human proteinases by micellar electrokinetic chromatography with anionic and nonionic surfactants, Electrophoresis, (2000), vol. 21, pp. 1985-1991.

Smith et al., Micellar electrokinetic capillary chromatography with in situ charged micelles IV. Influence of the nature of the alkylglycoside surfactant, Journal of Chromatography, (1994), vol. 685, pp. 131-143.

Smith et al., Micellar Electrokinetic Capillary Chromatography with in Situ Charged Micelles. 1. Evaluation of N-D-Gluco-N-methylalkanamide Surfactants as Anionic Borate Complexes, Anal. Chem., (1994), vol. 66, pp. 1119-1133.

Rassi, Chiral glycosidic surfactants for enantiomeric separation in capillary electrophoresis, Journal of Chromatography, (2000), vol. 875, pp. 207-233.

Terabe, Selectivity manipulation in micellar electrokinetic chromatography, Journal of Pharmaceutical & Biomedical Analysis, (1992), Vo. 10, Nos. 10-12, pp. 705-715.

Ahuja, et al., Infinite Elution Range in Micellar Electrokinetic Capillary Chromatography Using a Nonionic/Anionic Mixed Micellar System, Anal. Chem., (1995), vol. 67, pp. 26-33.

Burns et al., Predictions of Micelle-Water Partition Coefficients and Retention in Micellar Electrokinetic Chromatography from Solute Structure. 2. Fragmental Constant Approach, Anal. Chem., (2004), vol. 76, pp. 5451-5458.

Kelly et al., Prediction of Retention in Micellar Electrokinetic Chromatography from Solute Structure. 1. Sodium Dodecyl Sulfate Micelles, Anal. Chem., (2001), vol. 73, pp. 6057-6062.

Terabe et al., Band Broadening in Electrokinetic Chromatography with Micellar Solutions and Open-Tubular Capillaries, Anal. Chem., (1989), vol. 61, pp. 251-260.

Saitoh et al., Equilibrium Study on Interactions between Proteins and Bile-Salt Micelles by Micellar Electrokinetic Chromatography, Analytical Sciences, (Aug. 1996), vol. 12, pp. 569-573.

Vernille et al., Sequence-Specific Oligonucleotide Purification Using Peptide Nucleic Acid Amphiphiles in Hydrophobic Interaction Chromatographym Biotechnol. Prog., (2004), vol. 20, pp. 1776-1782.

Vernille et al., Peptide Nucleic Acid (PNA) Amphiphiles: Synthesis, Self-Assembly, and Duplex Stability, Bioconjugate Chem., (2004), vol. 15, pp. 1314-1321.

Lau et al., Morphological Characterization of Self-Assembled Peptide Nucleic Acid Amphiphiles, J. Phys. Chem., (2006), vol. 110, pp. 9027-9033.

Bello et al., Capillary electrophoresis instrumentation as a bench-top viscometer, Journal of Chromatography, (1994), vol. 659, pp. 199-204.

Bowser et al., Monte Carlo Simulation of Error Propagation in the Determination of Binding Constants from Rectangular Hyperbolae. 1. Ligand Concentration Range and Binding Constant, J. Phys. Chem., (1998), vol. 102, pp. 8063-8071.

Natt et al., Lipocap: a Lipophilic Phosphoramidite-based Capping Reagent, Tetrahedron, (1997), vol. 53, No. 28, pp. 9629-9636.

Nielsen et al., Application of 2-cyanoethyl N,N,N',N'-tetraisopropylphosphorodiamidite for in situ preparation of deoxyribonucleoside phosphoramidites and their use in polymer-supported synthesis of oligodeoxyribonucleotides, Nucleic Acids Research, (1986), vol. 14, No. 18, pp. 7391-7403.

Sinyakov et al., Functionalization of the Oligonucleotides Containing an Internucleotide Phosphoramidate Bond, Russian Journal of Bioorganic Chemistry, (2003), vol. 29, No. 1, pp. 88-90.

Gardner et al., Comparative Kinetics of Nucleotide Analog Incorporation by Vent DNA Polymerase, The Journal of Biological Chemistry, (2004), vol. 279, No. 12, pp. 11834-11842.

Gardner et al., Acyclic and dideoxy terminator preferences denote divergent sugar recognition by archaeon and Taq DNA polymerases, Nucleic Acids Research, (2002), vol. 30, No. 2, pp. 605-613.

Gardner et al., Determinants of nucleotide sugar recognition in an archaeon DNA polymerase, Nucleic Acids Research, (1999), vol. 27, No. 12, pp. 2545-2553.

Desruisseaux et al., Electrophoresis of Composite Molecular Objects. 2. Competition between Sieving and Frictional Effects in Polymer Solutions, Macromolecules (2001), vol. 34, pp. 5280-5286.

Desruisseaux et al., On Using DNA-Trapping Electrophoresis to Increase the Resolution of DNA Sequencing Gels, Macromolecules, (1998), vol. 31, pp. 6499-6505.

Beckers et al., The preparation of background electrolytes in capillary zone electrophoresis: Golden rules and pitfalls, Electrophoresis, (2003), vol. 24, pp. 518-535.

Ren et al., Applications of Short-Chain Polydimethylacrylamide as Sieving Medium for the Electrophoretic Separation of DNA Fragments and Mutation Analysis in Uncoated Capillaries, Analytical Biochemistry, (1999), vol. 276, pp. 188-194.

Allawi et al., Thermodynamics and NMR of Internal G-T Mismatches in DNA, Biochemistry, (1997), vol. 36, pp. 10581-10594.

Amaral et al., Nematic Domain in the Sodium Lauryl Sulfate/Water/Decanol System, J. Phys. Chem., (1988), vol. 92, pp. 6094-6098.

Bailey et al., pH effects on micelle-water partitioning determined by micellar electrokinetic chromatography, Journal of Chromatography, (1999), vol. 852, pp. 559-571.

Brown et al., Size and Shape of Nonionic Amphiphile Micelles: NMR Self-Diffusion and Static and Quasi-Elastic Light-Scattering Measurements on C12 E5 C12 E7 and C12 E8 in Aqueous Solution, J. Phys. Chem, (1988), vol. 92, pp. 6086-6094.

Bunton et al., Hydrophobic and Coulombic Interactions in the Micellar Binding of Phenols and Phenoxide Ions, The Journal of Physical Chemistry, (1979), vol. 83, No. 6, pp. 680-683.

Castoldi et al., A sensitive array for microRNA expression profiling (miChip) based on locked nucleic acids (LNA), RNA, (2006), vol. 12, No. 5, pp. 1-8.

Chu et al., Characterization of nanoparticles by scattering techniques, Journal of Nanoparticle Research, (2000), pp. 29-41.

Desruisseaux et al., Electrophoresis of Composite Molecular Objects. 1. Relation between Friction, Charge, and Ionic Strength in Free Solution, Macromolecules, (2001), vol. 34, pp. 44-52.

Egholm et al., PNA hybridizes to complementary oligonucleotides obeying the Watson-Crick hydrogen-bonding rules, Nature, (Oct. 7, 1993), vol. 365.

Galantini et al., An Integrated Study of Small-Angle X-ray Scattering and Dynamic Light Scattering on Cylindrical Micelles of Sodium Glycodeoxycholate, J. Phys. Chem., (2004), vol. 108, pp. 3078-3085.

Gitler et al., Nonpolar Contributions to the Rate of Nucleophilic Displacements of p-Nitrophenyl Esters in Micelles, Journal of the American Chemical Society, (Aug. 28, 1968), vol. 90, No. 18, pp. 5005-5009.

Gore et al., Self-Assembly of Model Collagen Peptide Amphiphiles, Langmuir, (2001), vol. 17, pp. 5352-5360.

Hartgerink et al., Self-Assembly and Mineralization of Peptide-Amphiphile Nanofibers, Science, (Nov. 23, 2001), vol. 294, pp. 1684-1688.

He et al., Comparison of Small-Angle Scattering Methods for the Structural Analysis of Octyl-B-maltopyranoside Micelles, J. Phys. Chem., (2002), vol. 106, pp. 7596-7604.

Imae et al., Structures of Fibrous Supramolecular Assemblies Constructed by Amino Acid Surfactants: Investigation by AFM, SANS, and SAXS, Journal of Colloid and Interface Science, (2000), vol. 225, pp. 285-290.

Long et al., Characterization of Lecithin-Taurodeoxycholate Mixed Micelles Using Small-Angle Neutron Scattering and Static and Dynamic Light Scattering, J. Phys. Chem., (1994), vol. 98, pp. 4402-4410.

Lyko et al., Quantitative analysis of DNA methylation in chronic lymphocytic leukemia patients, Electrophoresis, (2004), vol. 25, pp. 1530-1535.

Marques et al., Sequence-Specific Binding of DNA to Liposomes Containing Di-Alkyl Peptide Nucleic Acid (PNA) Amphiphiles, Langmuir, (2005), vol. 21, pp. 2488-2494.

(56) References Cited

OTHER PUBLICATIONS

McCormick et al., A theoretical study of the possible use of electroosmotic flow to extend the read length of DNA sequencing by end-labeled free solution electrophoresis, Electrophoresis, (2006), vol. 27, pp. 1693-1701.

Mehl et al., Viscosity and the Shape of Protein Molecules, Science, (Aug. 9, 1940), vol. 92, No. 2380, pp. 132-133.

Mikkers et al., Concentration Distributions in Free Zone Electrophoresis, Journal of Chromatography, (1979), vol. 169, pp. 1-10.

Nielsen, Peptide Nucleic Acid. A Molecule with Two Identities, Acc. Chem. Res., (1999), vol. 32, pp. 624-630.

Nielsen et al., Sequence-Selective Recognition of DNA by Strand Displacement with a Thymine-Substituted Polamide, Reports, (Dec. 6, 1991), vol. 254, pp. 1497-1500.

Paradies, Shape and Size of a Nonionic Surfactant Micelle. Triton X-100 in Aqueous Solution, J. Phys. Chem., (1980), vol. 84, pp. 599-607.

Pedersen, Analysis of small-angle scattering data from colloids and polymer solutions: modeling and least-squares fitting, Advances in Colloid and Interface Science, (1997), vol. 70, pp. 171-210.

Pillai et al., Inhibition of Translational Initiation by Let-7 MicroRNA in Human Cells, Science, (Sep. 2, 2005), vol. 309, pp. 1573-1576.

Quirino et al., Exceeding 5000-Fold Concentration of Dilute Analytes in Micellar Electrokinetic Chromatography, Science, (Oct. 16, 1998), vol. 282, pp. 465-468.

Quirino et al., On-line concentration of neutral analytes for micellar electrokinetic chromatography I. Normal stacking mode, Journal of Chromatography, (1997), vol. 781, pp. 119-128.

Ratilainen et al., Thermodynamics of Sequence-Specific Binding of PNA to DNA, Biochemistry (2000), vol. 39, pp. 7781-7791.

Ratilainen et al., Hybridization of Peptide Nucleic Acidm Biochemistry, (1998), vol. 37, pp. 12331-12342.

Sanchez et al., Linear-After-The Exponential (LATE)-PCR: An advanced method of asymmetric PCR and its uses in quantitative real-time analysis, PNAS, (Feb. 17, 2004), vol. 101, No. 7, pp. 1933-1938.

Santalucia, A unified vew of polymer, dumbbell, and oligonucleotide DNA nearest-neighbot thermodynamics, Proc. Natl. Acad. Sci., (Feb. 1998), vol. 95, pp. 1460-1465.

Shimizu et al., Self-assembling properties of synthetic peptidic lipids, Biochimica et Biophysica Acta, (1993), vol. 1147, pp. 50-58.

Stellwagen et al., Determining the electrophoretic mobility and translational diffusion coefficients of DNA molecules in free solution, Electrophoresis, (2002), vol. 23, pp. 2794-2803.

Thomas et al., Growth of Mixed Nonionic Micelles, Langmuir, (1997), vol. 13, pp. 209-218.

Tomac et al., Ionic Effects on the Stability and Conformation of Peptide Nucleic Acid Complexes, J. Am. Chem. Soc., (1996), vol. 118, pp. 5544-5552.

Won et al., Protein polymer drag-tags for DNA separations by end-labeled free-solution electrophoresis, Electrophoresis, (2005), vol. 26, pp. 2138-2148.

Vester et al., LNA (Locked Nucleic Acid): High-Affinity Targeting of Complementary RNA and DNA, Biochemistry, (Oct. 26, 2004), vol. 43, No. 42, pp. 13233-13241.

Albrecht et al. "A 265-Base DNA Sequencing Read by Capillary Electrophoresis with No Separation Matrix" (2011) Anal. Chem. 83:509-515.

Blake, RD, et al. "Thermodynamic effects of formamide on DNA stability" (1996) Nucleic Acids Res. 24(11):2095-2103.

Figeys, D, et al., "Pseudo-coulometric loading in capillary electrophoresis DNA sequencing", (1996) J. Chromatography A 744:325-31.

Rosenblum, BB, et al. "Improved single-strand DNA sizing accuracy in capillary electrophoresis" (1997) Nucleic Acids Res. 25(19):3925-3929.

* cited by examiner

TRANSIENTLY BONDING DRAG-TAGS FOR SEPARATION MODALITIES

CROSS REFERENCE TO RELATED APPLICATION

This application claims priority to U.S. Provisional Patent Application No. 60/936,728, filed Jun. 22, 2007, entitled "Rapid DNA Sequencing Using Alkylated Oligomers Transiently Bound to Surfactant Micelles in Free-Solution Electrophoresis", the disclosure of which is hereby incorporated by reference in its entirety.

STATEMENT REGARDING FEDERALLY SPONSORED RESEARCH

This invention was made with United States government support under United States Air Force Office of Scientific Research, Grant Number F49620-03-1-0153 and National Science Foundation, Grant Number BES-0093538. The government has certain rights in this invention.

BACKGROUND OF THE INVENTION

1. Field of the Invention

The invention relates to transiently binding a drag-tag to a molecule during a separation modality.

2. Description of Related Art

The ultimate success of a DNA sequencing methodology is determined by both the resolving power of the technique itself and its sensitivity to small differences in migrational velocity over a broad range of sequencing fragment lengths. For direct comparison of sequencing efficiency between various sequencing methodologies, it is often convenient to cite the length of read ("LOR")/unit time, usually in the number of called bases/day. Current capillary gel electrophoresis ("CGE")-based separation approaches have a LOR of approximately 500 to 600 bases with run times on the order of 2.5 hours. This would translate into approximately 5,000 bases/day for a single capillary instrument. For a 96 capillary array, this value approaches 500,000 bases/day, clearly indicating the advantage of massively parallel separations. This LOR is used as an indication of a technique's sequencing capacity. In CGE-based techniques, the major obstacle to longer sequencing read lengths is diffusion band broadening, a result of the long run times required to avoid biased reptation.

End labeled free solution electrophoresis (ELFSE) is a DNA separation modality capable of breaking the charge-to-friction ratio of DNA in a gel- or polymer-free context. At the foundation of this particular technique lies the notion that by appending a drag inducing entity (i.e. a "drag-tag"), predominantly one with little or no charge, the charge-to-friction symmetry of the DNA target can be broken, and the resulting DNA fragment can be separated. Since DNA acts as a free-draining coil, the electrophoretic mobility of DNA can roughly be described by q/f, or its charge-to-friction ratio, where q is the net charge on the molecule and f is the molecular friction coefficient. By covalently attaching an uncharged drag-tag to the DNA target, the friction induced by the pendant drag-tag moiety decreases the electrophoretic mobility through an increase in the hydrodynamic friction of the resulting complex. The drag-tag/DNA complex thereby possesses a charge equivalent to the DNA itself, while the combined hydrodynamic friction of the drag-tag/DNA complex is increased by the hydrodynamic friction of the entire complex, including the drag-tag.

Since the inception of ELFSE methods, a number of obstacles remain to be overcome for the successful application of this methodology. Since ELFSE-based approaches separate through inherently different physical mechanisms, biased reptation is not a concern, and substantially higher electric field strengths (and the short run times that would result) are achievable, representing an opportunity for improved separation performance. Unfortunately, there are entirely different limitations with ELFSE. The lack of sufficiently large, monodispersed polymeric drag-tags currently limits the achievable LOR for ELFSE based approaches to around 125 bases.

SUMMARY OF THE INVENTION

Until now, limitations on the ability to produce large, monodispersed drag-tags, has limited the applicability of methods such as ELFSE. This problem is resolved by the present invention, which transiently attaches drag-tags to the DNA fragment, as opposed to covalently attaching polydispersed polymers thereto. The dynamic nature of a drag-tag renders these separation modalities immune to the aggressive band broadening effects of drag-tag polydispersity and it is the transient nature of these interactions that offers the most distinct advantage over traditional ELFSE based approaches.

Therefore, if monodispersion of drag-tags is not feasible, the polydispersed drag-tags will randomly interact with a molecule. Consequently, the net effect of random interactions between drag-tags of different size eliminates the need for monodispersed drag-tags.

In some non-limiting embodiments, the invention generally relates to the concept of transiently binding a drag-tag to a molecule during a separation modality, such as electrophoresis. The separation modality occurs in the presence of a running buffer. The molecule comprises at least one polar moiety and at least one lipophilic moiety. The running buffer comprises a drag-tag. The drag-tag comprises a structure. The structure comprises a surfactant, a polymer or combinations thereof. During electrophoresis, for example, the molecule moves by the electrostatic force between the polar moiety and the electric field. During at least a portion of this movement, the lipophilic moiety hydrophobically interacts with the drag-tag. Thermal motion or an electrostatic force eventually breaks the hydrophobic interaction, thereby freeing the lipophilic moiety from the drag-tag and enabling the lipophilic moiety to interact with a second, different drag-tag.

In some non-limiting embodiments, the invention comprises a running buffer comprising a drag-tag. The drag-tag comprises a structure. The structure can be selected from the group consisting of a liposome, a micelle, a solid particle, a carbon nanotube, and an oil-in-water emulsion. The oil-in-water emulsions can be micro-emulsions or nano-emulsions. The structure comprises a surfactant, a polymer or a combination thereof. In embodiments where the structure is a solid particle or a carbon nanotube, the solid particle or carbon nanotube is coated with the surfactant, the polymer or combinations thereof.

In some non-limiting embodiments, the present invention comprises a molecule comprising at least one lipophilic moiety. In some embodiments, the molecule comprises a plurality of lipophilic moieties. The molecule comprises a nucleoside analog. The nucleoside analog comprises a sugar moiety having a 5' end carbon and a 3' end carbon, and a lipophilic moiety. The lipophilic moiety can be bonded to the 5' end, the 3' end or elsewhere on the sugar moiety. The lipophilic moiety can be bonded to the molecule by a linking group.

In some non-limiting embodiments, the molecule comprises a nucleic acid analog. The nucleic acid analog comprises a sugar moiety having a 5' end carbon and a 3' end carbon, and a lipophilic moiety. The lipophilic moiety can be bonded to the 5' end, 3' end or elsewhere on the sugar moiety.

In some non-limiting embodiments, the molecule comprises a protein-detergent complex. The protein-detergent complex comprises at least one protein and at least one lipophilic moiety bonded to at least a portion of the protein.

In some non-limiting embodiments, the invention comprises a lipophilic moiety comprising an alkyl group. The alkyl group can be selected from the group consisting of an octyl, a nonyl, a decyl, an undecyl, a dodecyl, a tridecyl, a tetradecyl, a pentadecyl, a hexadecyl, a heptadecyl, an octadecyl, a nonadecyl, an icosyl, a henicosyl, a docosyl, a tricosyl and a tetracosyl group. The lipophilic moiety further comprises a first functional group attached to the alkyl group. The lipophilic moiety further comprises a second functional group capable of bonding to a molecule.

In some non-limiting embodiments, the invention comprises a method of transiently attaching a drag-tag to a molecule. The method comprises providing a molecule comprising a polar moiety and a lipophilic moiety. The molecule is moved through the running buffer described above.

In some non-limiting embodiments, the invention comprises a method of transiently attaching a drag-tag to a molecule. The method comprises providing a molecule comprising a polar moiety and a lipophilic moiety. The molecule is placed in the running buffer described above. An electric field is applied to the running buffer for a period of time. A lipophilic interaction is formed between the lipophilic moiety and the drag-tag for a portion of the period of time. The lipophilic interaction is terminated during the period of time. The formation and termination of the lipophilic interaction are repeated through at least a portion of the period of time. The electric field is discontinued.

In some non-limiting embodiments, the invention comprises a method of separating molecules of different lengths. The method comprises providing at least two molecules, each molecule having a different length or size. Each molecule comprises a lipophilic moiety. The molecules are separated by electrophoresis using the running buffer described above.

In some non-limiting embodiments, the invention comprises a method of separating molecules of different lengths or size. The method comprises forming a hydrophobic interaction between a lipophilic moiety bonded to the molecule and a drag-tag. This hydrophobic interaction occurs during a separating modality, such as electrophoresis. The hydrophobic interaction is discontinued during the separation modality. The formation and discontinuation of the hydrophobic interaction is repeated throughout at least a portion of the separation modality. The molecules separate at least two different distances.

In some non-limiting embodiments, the invention comprises a method of measuring a hydrodynamic radius of a drag-tag. The method comprises providing a plurality of molecules. The plurality of molecules comprises a polar moiety and a lipophilic moiety, and each molecule comprises an approximately equal molecular weight. The plurality of molecules is moved a distance in the running buffer described above. Consequently, the distance can be used to determine the hydrodynamic radius of the drag-tag. The molecule can be a nucleic acid analog(s) of known size(s) comprising at least one lipophilic moiety.

In some non-limiting embodiments, the invention comprises a method of separating a plurality of drag-tags having different hydrodynamic radiuses. The method comprises providing a plurality of molecules. The molecules comprise a polar moiety and a lipophilic moiety, and have approximately an equal molecular weight. The molecules also are capable of binding tightly to the drag-tags described above, wherein the drag-tags have different hydrodynamic radiuses. The molecules are separated in the running buffer described above, and consequently, the drag-tags are also separated by their hydrodynamic radius.

BRIEF DESCRIPTION OF THE DRAWING(S)

DETAILED DESCRIPTION OF THE INVENTION

Figure 1:
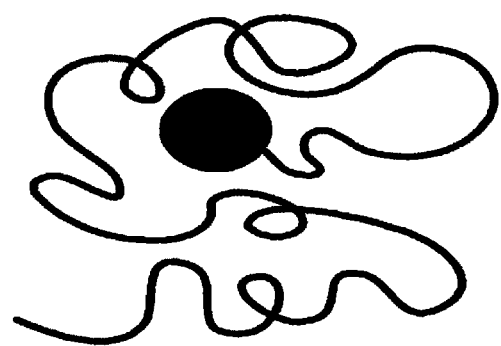
FIG. 1 is an illustration of a DNA molecule having a hydrodynamic drag-tag attached thereto.

Other than in the operating examples, or where otherwise indicated, all numbers expressing quantities of ingredients, thermal conditions, and so forth, used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values, inclusive of the recited values, may be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

Generally, the invention relates to separating molecules by transiently binding a drag-tag to a molecule during a separation modality. Non-limiting examples of separation modalities include ELFSE, micellular electrokinetic chromatography, microemulsion electrokinetic chromatography, liposome electrokinetic chromatography, and capillary electrophoresis.

This invention is captured by several embodiments. One embodiment of the invention is a method of transiently binding a drag-tag to a molecule. Another embodiment of the invention is a molecule comprising a lipophilic moiety. Another embodiment of the invention is a lipophilic moiety. Another embodiment of the invention is a method of measuring a hydrodynamic radius of a drag-tag. Another embodiment of the invention is a method of separating a plurality of drag-tag by their hydrodynamic radiuses. Another embodiment of the invention is a running buffer.

Transiently Attaching a Drag-Tag to a Molecule

A non-limiting embodiment of the invention is a method of transiently binding a drag-tag to a molecule. The method comprises providing a molecule. The molecule comprises at least one polar moiety and at least one lipophilic moiety. The molecule is moved through a running buffer. The running buffer comprises a drag-tag.

Another non-limiting embodiment of the invention is a method of transiently binding a drag-tag to a molecule. The method comprises providing a molecule. The molecule comprises at least one polar moiety and at least one lipophilic moiety. The molecule is placed in a running buffer comprising a drag-tag. An electric field is applied to the running buffer for a period of time. During at least a portion of the period of time, a hydrophobic interaction is formed between the lipophilic moiety and the drag-tag. The hydrophobic interaction is terminated. The formation and termination of the hydrophobic interaction is repeated for at least a portion of the period of time. The electric field is discontinued.

Another non-limiting embodiment of the invention is a method of separating molecules. The method comprises providing a plurality of molecules having at least two different lengths. Each molecule comprises at least one polar moiety and at least one lipophilic moiety. The molecules are separated by a separation modality in a running buffer. The running buffer comprises a drag-tag.

Another non-limiting embodiment of the invention is a method of separating molecules by their molecular weight or size. The method comprises providing a plurality of molecules. Each molecule comprises at least one polar moiety and at least one lipophilic moiety. At least a portion of the molecules is placed in a running buffer comprising a drag-tag. An electric field is applied to the running buffer for a period of time. During at least a portion of the period of time, a hydrophobic interaction is formed between the lipophilic moiety and the drag-tag. The hydrophobic interaction is terminated. The formation and termination of the hydrophobic interaction is repeated for at least a portion of the period of time. The electric field is discontinued.

One of ordinary skill in the art would recognize a polar moiety of a molecule that would be useful in this embodiment. For example, if the molecule is a nucleic acid analog, the polar moiety would include a phosphate group found on the backbone of the nucleic acid. In another example, if the molecule is a protein-detergent complex, the polar moiety would include the amino acid(s) that provide a net charge to the protein/detergent complex at a particular pH.

In some non-limiting embodiments, the lipophilic moiety comprises an alkyl group. The alkyl group can be linear and/or saturated. It can comprise at least about 8 carbon atoms, at least about 12 carbon atoms, no more than about 24 carbon atoms or no more than about 18 carbon atoms. For example, the alkyl group can be selected from the group consisting of an octyl, a nonyl, a decyl, an undecyl, a dodecyl, a tridecyl, a tetradecyl, a pentadecyl, a hexadecyl, a heptadecyl, an octadecyl, a nonadecyl, an icosyl, a henicosyl, a docosyl, a tricosyl and a tetracosyl group. The lipophilic moieties can also comprise fluorinated hydrocarbons or fluorocarbons. The fluorocarbons can be selected from the group consisting of $C_8F_{15}$, $C_{10}F_{19}$ and $C_{12}F_{23}$ and $C_6F_{13}$. In another embodiment, at least a portion of the plurality of molecules comprises a lipophilic moiety. Each lipophilic moiety can comprise approximately an equal number of carbon atoms.

Figure 6:
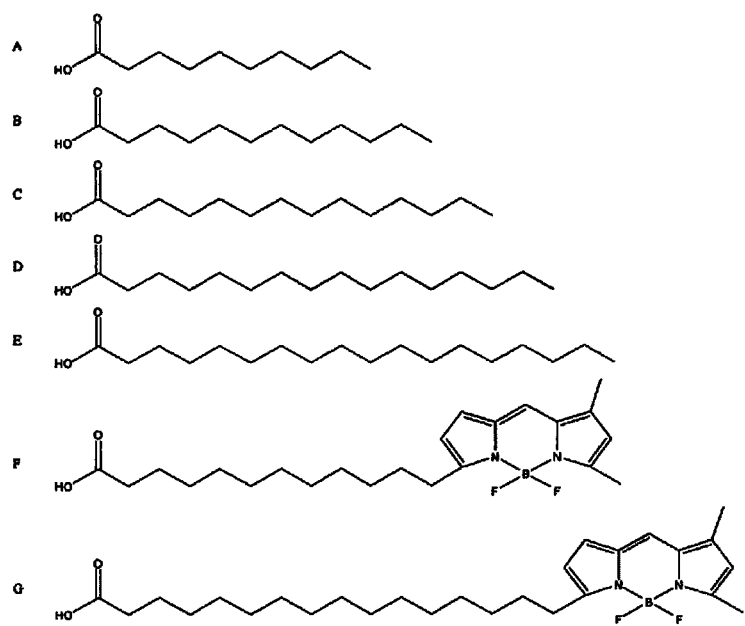
FIG. 6 illustrates the chemical structures of the various aliphatic groups successfully coupled to 5' amine labeled DNA oligonucleotides using the post-synthetic modification protocol. A) $C_{10}$ B) $C_{12}$ C) $C_{14}$ D) $C_{16}$ E) $C_{18}$ F) $C_{12}$-Bodipy-Fl G) $C_{16}$-Bodipy-Fl.
Figure 7:
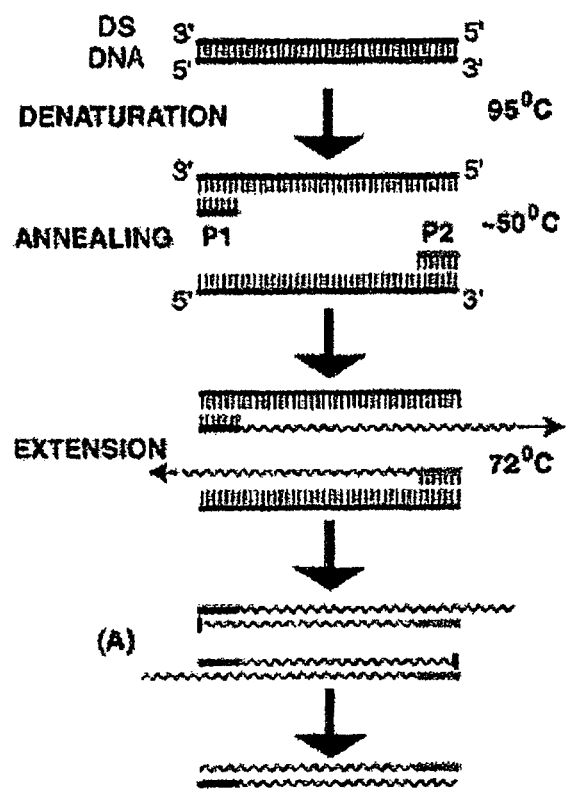
FIG. 7 is a schematic illustration of the polymerase chain reaction.

The lipophilic moiety can comprise a functional group. In some non-limiting embodiments, the functional group is a chromophore. In other non-limiting embodiments, the functional group is a fluorophore. In other non-limiting embodiments, the functional group is boron-dipyrromethene. For example, the lipophilic moiety can comprise a Bodipy fluorophore. Due to the uncharged-hydrophobic nature of the Bodipy fluorophore, fatty acid derivatives of Bodipy are well suited for the conjugation to DNA oligonucleotides to create a fluorescently labeled aDNA. The chemical structure of the numerous aliphatic groups successfully coupled to a DNA oligonucleotide may be found in FIG. 6. In other non-limiting embodiments, the functional group can comprise a radioactive atom, such a $^{32}P$ or $^{33}P$.

The lipophilic moiety can hydrophobically interact with a drag-tag. As used herein, the term "drag-tag" means a moiety that modifies the charge-to-friction ratio of a molecule. The charge-to-friction ratio of a molecule can be modified by increasing the friction coefficient. In this example, assuming that the charge of the molecule was negative, the charge-to-friction ratio would move closer to 0, or increase. Alternatively, if the charge was positive, the charge-to-friction ratio would likewise move closer to 0, or decrease. In some non-limiting embodiments, the drag-tag comprises a structure selected from the group consisting of a liposome, a micelle, a solid particle, a carbon nanotube, and an oil-in-water emulsion. The oil-in-water emulsions can be micro-emulsions or nano-emulsions. The structure can comprise a surfactant. The surfactant can be non-ionic, cationic, anionic, zwitterionic, or combinations thereof. Non-limiting examples of suitable non-ionic surfactants include acetylenic glycols, alkanolamides, alkanolamines, alkyl β-D-glycopyranosides, alkyl phenols, alkylglucosides, alkylmonoglucosides, fatty acids, fatty alcohols, fatty esters, glycerol esters, monododecyl ethers (such as $C_{12}E_5$, $C_{16}E_6$ and $C_{12}E_8$), phenol derivatives, poloxamers, poloxamines, polyoxyethylene acyl ethers, polyoxyethyleneglycol dodecyl ethers (such as Brij-35), sorbitols and sorbitan derivatives (such as Tween-20 and Tween-60), alkylphenol ethylene oxide condensates, alkyl ethylene oxide condensates, octylphenol ethylene oxide condensates (such as Triton X-100), fluoroalkylphenol ethylene oxide condensates, fluoroalkyl ethylene oxide condensates, partially fluorinated fluoroalkylphenol ethylene oxide condensates, partially fluorinated fluoroalkyl ethylene oxide condensates, fluorinated hydrocarbons (such as $C_8 F_{15}$, $C_{10} F_{19}$ and $C_{12} F_{23}$ and $C_6 F_{13}$), partially fluorinated hydrocarbons, fluorocarbon-based surfactants (such as Zonyl fluorosurfactants, Masurf FS-fluorosurfactants, Novec fluorosurfactants, and PEG-block-fluorocarbon copolymer fluorosurfactants) and combinations thereof. Non-limiting examples of suitable cationic surfactants include alkylamines, quaternary amines, imidazolines, dialkylamine oxides, gemini surfactants, and combinations thereof. Non-limiting examples of anionic surfactants include salts of multiple acids, salts of fatty acids, sodium dodecyl sulfates, bile acid salts, isethionates, salts of tall oil acids, alcohol phosphates, inorganic phosphates, sarcosine derivatives, alcohol sulfates, alkyl phenol sulfates, sulfated triglycerides, alpha-olefin sulfonates, linear alkylbenzene sulfonates, aromatic sulfonates, sodium alkyl sulfonates, sulfosuccinates, taurates, gemini surfactants, and combinations thereof. Non-limiting examples of zwitterionic surfactants include amino acids, betaines, imidazolines, imino acids, phospholipids, gemini surfactants, and combinations thereof.

In some embodiments, the structure can comprise a polymer. Non-limiting examples of suitable polymers include polyethylene oxide (PEO) polymers, polypropylene oxide (PPO) polymers, PEO-PPO block copolymers, PEO-PPO-PEO triblock copolymers, Pluronic-type polymers, hydrophobically modified PEO polymers, protein-based polymers, polypeptides, polypeptoids, polysaccarhides, hydrophobically modified polysaccarhides, cellulose derivatives, sodium carboxymethylcellulose, hydroxymethylcellulose, hydroxyethylcellulose, hydroxypropylcellulose, hydroxypropylmethyl cellulose, alkali-soluble associative (HASE) polymers, hydrophobically modified polyacrylamides, thermally responsive polymers, N-isopropylacrylamide (NTPAAm), poly(ethylene glycol) methylether acrylate (PEGMEA), tetraethylene glycol diacrylate (TEGDA), poly(ethylene glycol) dimethacrylate (EGDMA), N,N'-methylene-bis-acrylamide (NMBA), and combinations thereof.

The molecules can be any molecule that one skilled in the art would recognize as capable of being separated by a separation modality, such as electrophoresis. In some non-limiting embodiments of the invention, the molecule comprises a nucleic acid analog. The nucleic acid analog comprises at least one lipophilic moiety. In these embodiments, the polar moiety is the phosphate group in the backbone of the nucleic acid analog. The lipophilic moiety is an alkyl group that is bonded to the nucleic acid. In some non-limiting embodiments, the alkyl group is covalently bonded to the sugar moiety of the nucleic acid. In other non-limiting embodiments, the alkyl group is covalently bonded at the 3' end carbon or the 5' end carbon of the sugar moiety.

In another non-limiting embodiment of the invention, the molecule comprises a protein-detergent complex. The protein-detergent complex comprises at least one amino acid. The amino acid comprises a moiety that is the polar moiety. The protein-detergent complex further comprises at least one lipophilic moiety. The lipophilic moiety can be a detergent. The detergent can be selected from the group consisting of sodium dodecyl sulfate, sodium lauryl sulfate and combinations thereof. The protein-detergent complex can further comprise a protein denaturing agent. Non-limiting examples of a protein denaturing agents include urea and guanidinium hydrochloride. The lipophilic moiety forms a bond with the amino acid. The bond can be an ionic bond.

A certain embodiment of the invention is a method of separating a plurality of nucleic acids having at least two different lengths. This embodiment comprises providing at least two nucleic acids having different lengths. Each nucleic acid comprises a lipophilic moiety as described above. The nucleic acids can be separated by thermal motion or electrophoresis in a running buffer. The running buffer comprises a drag-tag.

Another embodiment of the invention is a method of separating nucleic acids of different lengths. This embodiment comprises forming a hydrophobic interaction between a lipophilic moiety bonded to a nucleic acid and a drag-tag during a separation modality. The hydrophobic interaction is discontinued during the separation modality. Optionally, the forming step and the discontinuing step are repeated.

In certain non-limiting embodiments, the lipophilic moiety can hydrophobically interact with a first drag-tag during a separation modality. The hydrophobic interaction is discontinued during the separation modality. Thereafter, the lipophilic moiety can hydrophobically interact with a second drag-tag tag during the separation modality. The hydrophobic interaction between the lipophilic moiety and the second drag-tag is discontinued. The formation and discontinuation of hydrophobic interactions can be repeated between numerous random drag-tags and the same lipophilic moiety.

The separation modality can be selected from the group consisting of end-labeled free solution electrophoresis (ELFSE), micellular electrokinetic chromatography, microemulsion electrokinetic chromatography, liposome electrokinetic chromatography, and capillary electrophoresis. Certain embodiments of the invention are devices comprising a power-source. The power-source is capable of generating electric fields of at least 100 V/cm, at least 500 V/cm, at least 1,000 V/cm, or at least 10,000 V/cm.

For convenience, the present invention is illustrated by the non-limiting ELFSE separation modality of DNA in a micelle-containing running buffer. A means to disrupt the insensitivity of the mobility to nucleic acid length is required to practice the invention. This can be accomplished by altering the hydrodynamic drag that the nucleic acid molecule possesses by separating the nucleic acid in a separation modality. Prior to this invention, it was assumed that the drag-tag had to be covalently bonded to the DNA fragment. Using this model, any polydispersity present in the size and/or shape of the drag-tag population would translate into deviations imparted to various DNA fragments of equal length, and subsequent loss of resolution in DNA sequencing. It was determined that a polydispersity value of 1.00001 was sufficient to virtually eliminate these deviations in DNA sequencing.

The influence that polydispersity has on the resolution of nucleic acid separation modality, such as modalities used for DNA sequencing, is most easily addressed by assuming that the drag-tag is an uncharged polymer consisting of $M_u$ identical, uncharged monomer units. Assuming that each monomer unit has a molecular weight defined as $fw_u$, the number average molecular weight, $M_n$, of the polymer is $M_n = M_u fw_u$. Provided that the polydispersity index (PDI) of the polymer is known, (PDI=$M_w/M_n$), and that the average molecular weight, $M_w$, of the polymer follows a normal distribution, the standard deviation of the molecular weight is $\sigma^2_{Mn} = M^2_n$ (PDI−1). The error introduced through polydispersity is expected to increase the temporal variance according to $\sigma^2_{t\_Total} = \sigma^2_{t\_Diff} + \sigma^2_{t\_Poly}$, where $\sigma^2_{t\,poly}$ poly is the temporal variance caused by polydispersity in the drag-tag molecular weight, calculated through propagation of error from $\sigma^2_{Mn}$ calculated as $$\sigma^2_{t\_Poly} = \sqrt{\left(\frac{\partial t(M)}{\partial M_n}\right)^2 (\sigma_{Mn})^2} = \left(\frac{1_D 1_T}{\mu_o V} \frac{\alpha}{M_c}\right)^2 (PDI - 1).$$

From these equations, the polydispersity value can be calculated according to $$R(M) = \sqrt{8\ln(2)} \sqrt{\frac{2D_1 1_T}{\mu_o V 1_D} \frac{(M_c + \alpha)^{5/2}}{\alpha^2} M_c + M_c(PDI - 1)}.$$

According to this equation, to bring the length of read (LOR) up to a value of 130, the PDI would have to be 1.00001. This has not heretofore been accomplished using the currently existing separation modalities.

Use of a transiently attached drag-tag has the advantage that increased sampling of a drag-tag during the separation results in increased monodispersity in the degree of hydrodynamic drag imparted by the tag. The hydrodynamic drag experienced by a particular DNA fragment and its subsequent electrophoretic mobility is the average of numerous interactions between different drag-tags. Provided that the number of interactions is sufficiently large, each DNA fragment of a specific length is expected to hydrophobically interact with an equivalent distribution of drag-tag morphologies and each fragment's resultant average electrophoretic mobility is expected to be equal. This does not imply that each population of DNA fragment lengths will experience the same number of interactions, since fragments moving more slowly would spend a longer time within the capillary. However, each DNA fragment of a specific length is expected to experience an equivalent number of interactions, and as a result, should hydrophobically interact with an approximately equivalent distribution of drag-tag morphologies.

The polydispersity resulting from x transient interactions, $PDI_x$ with a drag-tag possessing a polydispersity of PDI is given by $$PDI_x = \frac{\sigma^2_{Mnx}}{M_n^2} + 1,$$

where $\sigma_{Mnx}$ is the standard deviation in the population generated by sampling $M_n$ over x interactions. Provided $M_n$ is normally distributed, $\sigma_{Mnx}$ is equal to the standard error, SE, $$SE = \sigma_{Mnx} = \frac{\sigma_{Mn}}{\sqrt{x}}.$$

Figure 2:
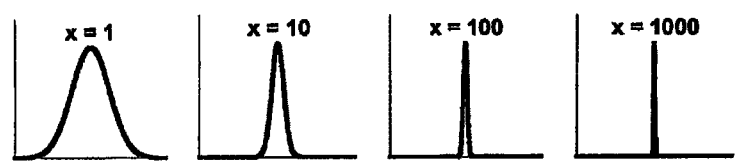
FIG. 2 is a chart demonstrating the impact of transient interactions on drag-tag polydispersity.

For a polymer drag-tag with a PDI=1.01, $PDI_{1000}$=1.00001, indicating that through the use of a transiently attached drag-tag, ELFSE-based separations for DNA sequencing are indeed feasible. An example of the probability distribution calculated from the predicted polydispersity for various numbers of interactions is shown in FIG. 2. Each figure represents the probability function distribution for x transient interactions. In this figure, the probability distribution is determined by the following formula:

$$f(x) = \frac{1}{SE\sqrt{2\pi}} \exp\left(\frac{-(x - \hat{x})^2}{2SE^2}\right).$$

It is readily observable that a sufficient number of interactions with even a moderately polydispersed plurality of drag-tags has the ability to render the effective drag induced by the tag virtually monodispersed. For applications in DNA sequencing, the size resolution factor, R(M), need only be adjusted slightly to account for transient interactions:

$$R(M) = \sqrt{8\ln(2)} \sqrt{\frac{2D_1 1_T}{\mu_o V 1_D} \frac{(M_c + \alpha)^{5/2}}{\alpha^2} M_c + M_c\left(\frac{PDI - 1}{x}\right)}.$$

Adopting identical experimental conditions as above and assuming PDI=1.01, a single, permanent interaction, predicts LOR=4 bases. For x=1000 interactions, the predicted LOR=131 bases. If the number of interactions approaches $1 \times 10^6$, LOR=457 bases, only three bases short of the value predicted for a perfectly monodispersed polymer drag-tag.

Implementing the notion of transiently attaching a polymer drag-tag is not immediately straightforward. If, for example, one were to rely on a physical interaction between an uncharged polymer and a DNA molecule, it is unlikely that there would be exactly one site of interaction on the DNA molecule at any given instance. If one were to rely on a specific interaction such as that afforded by the receptor-ligand pair streptavidin and biotin, it may be difficult to tune the binding strength such that there are a sufficient number of interactions to appreciably lower the effective polydispersity of the drag-tag. To circumvent this issue, the present inventors have determined that a lipophilic moiety can be appended to a molecule, for example a nucleic acid. Although the lipophilic moiety is not expected to impart a significant amount of drag to the DNA fragment, the transient interaction of that group with a large, uncharged surfactant micelle is believed to behave in an equivalent fashion to the polymeric drag-tag discussed above. Provided that the micelle is sufficiently large, with an equivalent drag of ~150 bases, and the lifetime of a DNA/micelle interaction is sufficiently short, the increase in effective monodispersity afforded by the transient nature of the interaction would lead to competitive DNA sequencing technologies using ELFSE.

The polyanionic character of nucleic acids renders them largely hydrophilic, and therefore limits its interaction with a micellular subphase. As a consequence, micelles have not been used for the separation of intact oligonucleotides. The use of hydrophobically modified nucleic acids promotes this DNA/micelle interaction, and is believed to be at least partially responsible for the separations achieved throughout this invention.

A nucleic acid can only interact with one of the two phases (aqueous phase or the micellular phase) at any instant and the interaction process can be modeled as an equilibrium reaction $DNA_{aq} + Mic \leftrightarrow DNA_m$. The propensity for a nucleic acid to interact with either phase can be predicted by $$[DNA_{mic}] = \frac{K[Mic][DNA_{Total}]}{1 + K[Mic]} \text{ and } [DNA_{aq}] = \frac{[DNA_{Total}]}{1 + K[Mic]},$$

where an equilibrium constant or partition coefficient, K, is defined as:

$$K \equiv \frac{[DNA_m]}{[DNA_{aq}][Mic]}$$

where $[DNA_m]$ and $[DNA_{aq}]$ are the concentrations of the DNA fragment in the micellular and aqueous phases respectively, and [Mic] is the concentration of micelles. These equations give an indication of the propensity of a DNA fragment to reside in either of the two phases, the aqueous phase or the micelle phase, provided the partition coefficient, K, is known.

The partition coefficient serves as an efficient measure of the interaction process. The poly-anionic character of DNA renders it sufficiently hydrophilic so that interaction with the micellular phase is highly unlikely. To promote micelle/DNA interaction, a hydrophobic group is attached to the DNA fragment in the form of a simple aliphatic carbon chain ranging in length from 8-24 carbons, 12-24 carbons, 8-18 carbons or 12-18 carbons. It is believed that a carbon tail ranging as short as 8 carbons, and as long as 24 carbons would be effective in various cases. Upon addition of a substantially hydrophobic group, such as the $C_{18}$ alkane chain, the partition coefficient, K, is approximately 1500, indicating the fraction of time the modified DNA spends attached to the micellular phase ($f_{mic}$) is nearly one.

Once the extent of interaction with a micellular phase is known, the effective mobility, $\mu_{eff}$, of the DNA population can be calculated. This is accomplished by assuming that the DNA's effective mobility is simply a weighted average, weighted by the fractional micellular interaction; of the intrinsic mobility of the fragment, $\mu_{DNA}$; and the mobility of the micelle, $\mu_{mic}$; according to $\mu_{eff} = f_{aq} \cdot \mu_{DNA} + f_{mic} \cdot \mu_{mic}$. Thus, the effective mobility can be calculated according to $$\mu_{eff} = \frac{1}{1 + K[Mic]} \cdot \mu_{DNA} + \frac{K[Mic]}{1 + K[Mic]} \cdot \mu_{mic}.$$

Although an uncharged, non-ionic surfactant micelle, ($\mu_{mic}=0$), was used for the majority of separations described herein, this quantity is more appropriately defined as the mobility of a micelle while it is interacting with the DNA, rather than the micelle mobility alone. Since the DNA has a substantial electrophoretic mobility, the mobility of the micelle while interacting with the DNA fragment does not reflect the intrinsic mobility of the micelle itself. This micelle/DNA complex mobility is governed by physics similar to a covalently attached drag-tag.

Moreover, charged surfactants may be used, so long as the mobility of the drag-tag differs from the mobility of the molecule. For example, charged micelles can be used in free-solution separation of alkylated DNA analogs, so long as the DNA analogs have a greater electrophoretic mobility than the micelles.

There are a few considerations that need to be taken into account to permit an accurate prediction of the effective or average electrophoretic mobility of the DNA fragment. One of the main considerations is the fact that the presence of micelles within the running buffer increases its viscosity. Since electrophoretic mobility scales as $1/\eta$, this has the impact of decreasing the experimentally measured electrophoretic mobility of the hydrophobically tagged DNA molecule. However, if every DNA fragment present in the sample is labeled with the hydrophobic aliphatic tail, the intrinsic mobility of the DNA fragment in the absence of a micelle is not experimentally observable. This is due to the fact that the only measurable indication is the effective, or average, electrophoretic mobility, and as a consequence, neither $\mu_{DNA}$ nor $\mu_{mic}$ is measured directly. Corrections for viscosity are taken into account by the following equations:

$$\mu_{eff} = \frac{\mu°_{DNA} + K[Mic]\mu°_{mic}}{(1 + K[Mic])(1 + C_{visc}[Mic])};$$

where $$\mu_{DNA} = \frac{C\varepsilon\zeta_{DNA}}{\eta}$$

(C is a constant, $\epsilon$ is the permittivity of the running buffer, $\zeta_{Dup}$ is the zeta potential of the duplex and $\eta$ is the viscosity of the running buffer); the new intrinsic mobility, $$\mu°_{DNA}, \text{ is } \frac{\mu_{DNA}}{\mu°_{DNA}} = \frac{\eta_o}{\eta};$$

and $\eta_o$ is the viscosity of the surfactant-free running buffer.

$$\mu_{eff} = \frac{\mu°_{DNA} + K[Mic]\mu°_{mic}}{(1 + K[Mic])(1 + C_{visc}[Mic])}$$

directly relates the experimentally measurable effective or average mobility of the hydrophobically labeled DNA to the total concentration of micelles in the running buffer through the partition coefficient K, and the micelle mobility $\mu°_{mic}$. In an effort to determine these two coefficients, $$\mu_{eff} = \frac{\mu°_{DNA} + K[Mic]\mu°_{mic}}{(1 + K[Mic])(1 + C_{visc}[Mic])}$$

can be linearized to allow for significantly more a straightforward parameter estimation with negligible loss in parameter accuracy as $$\frac{1}{\mu_{eff}(1 + C_{visc}) - \mu°_{DNA}} = \frac{1}{(\mu°_{mic} - \mu°_{DNA})} + \frac{1}{K(\mu°_{mic} - \mu°_{DNA})} \frac{1}{[M]}.$$

By conducting a series of electrophoretic separations, each at a different surfactant concentration, the effective mobility of the DNA fragment can be determined. When combined with knowledge of the viscosity constant and the intrinsic mobility of the DNA fragment, measured in the absence of surfactant micelles, the above equation can readily be solved by linear regression.

The aliphatic tail is likely to have no detectable impact on the electrophoretic mobility of the nucleic acid analog. This is a result of the fact that the amount of drag associated with 24 carbons is not sufficient to alter the electrophoretic mobility of the substantially larger DNA fragment. This assumption is valid for all but the shortest DNA fragments. The remainder of the separation can be described quite simply. While a hydrophobically modified DNA target is interacting with a micelle of size α, it would possess an electrophoretic mobility defined by $\mu°_{mic}$. The value of $\mu°_{mic}$ is determined by the combined drag of the uncharged surfactant micelle, the intrinsic mobility of the DNA fragment, $\mu°_{DNA} = \mu_o$, and the length of the DNA fragment, $M_c$, according to $$\mu = \mu_o \frac{M_c}{M_c + \alpha}.$$

For the fraction of the separation that the DNA fragment is not interacting with the micellular phase, the DNA would migrate at its free-solution electrophoretic mobility, $\mu°_{DNA}$. Thus, the effective mobility of alkylated DNA analogs can be calculated according to $$\mu_{eff} = \frac{\mu°_{DNA}(M_c(1 + K[Mic]) + \alpha)}{(1 + K[Mic])(1 + C_{visc}[Mic])(M_c + \alpha)}.$$

The size resolution factor R(M) can accurately evaluate the impact that of the micellular interaction on the resolution of DNA fragments. The impact that polydispersity of micelles is expected to be negligible provided there are a sufficient number of interactions between the DNA fragment and the micellular drag-tag. This can be confirmed by calculating R(M) according to the following equation:

$$R(M) = R_o \left( \frac{\sqrt{M_c + \alpha}}{K[Mic]\sqrt{M}} + \right)^{1/2} \frac{(M_c + \alpha)^{5/4}}{K[Mic]\alpha M_c^{1/4}}(M_c(1 + K[Mic]) + \alpha)^{3/2},$$

where $$R_o \equiv \sqrt{\frac{16\ln(2)D_1 1_T}{\mu°_{DNA} V 1_D}}(1 + C_{Visc}[Mic]).$$

Applying hypothetical experimental conditions where E=333 V/cm, $l_D$=34 cm, $D_1$=3.2×10$^{-6}$ cm$^2$/s, $\mu°_{DNA}$=−1.95× 10$^4$ cm$^2$/Vs and α=24, the predicted LOR is 127 bases. At a micelle concentration of 0.1 mM, with K=1000 mM$^{-1}$ and $C_{visc}$=0.5 mM$^{-1}$, the predicted LOR is 125 bases. For α=150 and E=1000 V/cm, a transient attachment of a surfactant micelle predicts a LOR=447 bases, only 13 bases below the 460 bases, which is the predicted LOR for a covalently attached monodispersed drag-tag. This deviation is due in large part to the contribution that the increased solution viscosity has on the separation, and if viscosity effects are assumed to be negligible, the LOR would be 455 bases. This is readily explainable by the fact that, all, or almost all of DNA fragments are expected to be interacting with a surfactant micelle at any given instant.

Nucleoside Analogs and Nucleic Acid Analogs

Another embodiment of the invention is a nucleoside analog. The nucleoside analog comprises a nucleoside bonded to a lipophilic moiety. The nucleoside is a glycosylamine comprising a sugar moiety selected from the group consisting of a ribose or a deoxyribose, and a nucleobase attached to the sugar moiety. The nucleobase can be selected from the group consisting of adenosine, cytidine, guanosine, thymidine and uridine.

The sugar moiety comprises a 3' end carbon and a 5' end carbon. The lipophilic moiety can be bonded or directly bonded to a sugar. In one non-limiting embodiment, the lipophilic moiety is bonded or directly bonded to the 3' end carbon. In another non-limiting embodiment, the lipophilic moiety is bonded or directly bonded to the 5' end carbon. In one embodiment, the nucleoside analog comprises a plurality of lipophilic moieties. The lipophilic moiety can be bonded to the nucleoside by a linking group. The linking group is a group that bonds the lipophilic moiety and the nucleoside. One skilled in the art would recognize groups that bond between lipophilic moieties and nucleosides. Non-limiting examples of linking groups include an amide, a phosphoramidite bond and a phosphodiester bond.

The lipophilic moiety can comprise an alkyl group. The alkyl group can be linear and/or saturated. It can comprise at least about 8 carbons, at least about 12 carbons, no more than about 24 carbons or no more than about 18 carbons. The alkyl group can be selected from the group consisting of an octyl, a nonyl, a decyl, an undecyl, a dodecyl, a tridecyl, a tetradecyl, a pentadecyl, a hexadecyl, a heptadecyl, an octadecyl, a nonadecyl, an icosyl, a henicosyl, a docosyl, a tricosyl and a tetracosyl group. The lipophilic moieties can also comprise fluorinated hydrocarbons or fluorocarbons. The fluorocarbons can be selected from the group consisting of $C_8 F_{15}$, $C_{10} F_{19}$ and $C_{12} F_{23}$ and $C_6 F_{13}$.

The lipophilic moiety can optionally comprise a functional group. In some non-limiting embodiments, the functional group is a chromophore. In other non-limiting embodiments, the functional group is a fluorophore. In other non-limiting embodiments, the functional group is boron-dipyrromethene. In other non-limiting embodiments, the functional group comprises a radioactive atom. For example, the functional group can comprise a radioactive phosphorus, such as $^{32}P$ or $^{33}P$.

Another embodiment of the invention is a nucleic acid analog. The nucleic acid analog comprises at least one nucleoside analog described above.

In some embodiments, the present invention comprises a primer for a polymerase chain reaction comprising the nucleic acid analog.

Bonding the lipophilic moiety to the 5' end or the 3' end means bonding the lipophilic moiety to the 5' carbon or 3' carbon, or bonding the lipophilic moiety to a 5' nucleoside or a 3' nucleoside. Bonding the lipophilic moiety to the nucleoside, for example the 5' nucleoside or the 3' nucleoside, can occur anywhere on the nucleoside.

Lipophilic Moiety

Some embodiments of the invention comprise a lipophilic moiety. The lipophilic moiety comprises an alkyl group. The alkyl group can be linear and/or saturated. It can comprise at least about 8 carbons, at least about 12 carbons, no more than about 24 carbons or no more than about 18 carbons. The alkyl group may be selected from the group consisting of an octyl, a nonyl, a decyl, an undecyl, a dodecyl, a tridecyl, a tetradecyl, a pentadecyl, a hexadecyl, a heptadecyl, an octadecyl, a nonadecyl, an icosyl, a henicosyl, a docosyl, a tricosyl and a tetracosyl group. The lipophilic moieties can also comprise fluorinated hydrocarbons or fluorocarbons. The fluorocarbons can be selected from the group consisting of $C_8 F_{15}$, $C_{10} F_{19}$ and $C_{12} F_{23}$ and $C_6 F_{13}$.

The lipophilic moiety comprises a first functional group. The first functional group can be useful in detecting a molecule. The method of detection can be visual or by radiograph. In some non-limiting embodiments, the functional group is a chromophore. In other non-limiting embodiments, the functional group is a fluorophore. In other non-limiting embodiments, the functional group is boron-dipyrromethene. In other non-limiting embodiments, the functional group comprises a radioactive atom.

The lipophilic moieties comprise a second functional group. The second functional group is useful in attaching the lipophilic moieties to a molecule. By way of example, the second functional group can be selected from the group consisting of an alcohol, an amine and a carboxylic acid.

Measuring a Hydrodynamic Radius of a Drag-Tag

In some embodiments, the invention is a method of measuring a hydrodynamic radius of a drag-tag. The method comprises providing a plurality of molecules. Each molecule comprises a polar moiety, and a lipophilic moiety. The molecules comprise an approximately equal molecular weight, or an equal molecular weight. The molecules can also comprise an approximately equal charge, or an equal charge. For example, if the molecule comprises a plurality of nucleic acid analogs as described above, at least a portion of the plurality of the nucleic acid analogs would have an approximately equal molecular weight, or an equal molecular weight. This can be achieved by providing a portion of nucleic acid analogs having an approximately equal number of nucleotides, or an equal number of nucleotides. The nucleic acid analogs of this example would likewise have an approximately equal charge, or an equal charge because the net charge on a nucleic acid is approximately equal or equal.

The plurality of molecules is moved by a separation modality a distance in a running buffer comprising the drag-tag. The drag-tag comprises a structure having an unknown hydrodynamic radius. The structure comprises a surfactant, a polymer or combinations thereof. The lipophilic moieties on the drag-tags hydrophobically interact with the molecule during at least a portion of the separation modality. Consequently, the distance that the molecules move is related to the hydrodynamic radius of the drag-tag. From this distance, the hydrodynamic radius of the drag-tag can be determined. Generally, drag-tags in an aqueous suspension with hydrodynamic radius between 1 nm and 1,000 nm can be assayed using the method.

Separating Drag-Tags Based on Their Hydrodynamic Radius.

In some embodiments, the invention is a method of separating a plurality of drag-tags having different hydrodynamic radiuses. The method comprises providing a plurality of molecules. The molecules comprise a polar moiety and a lipophilic moiety. The molecules comprise an approximately equal molecular weight, or an equal molecular weight. The molecules can also comprise an approximately equal charge, or an equal charge. The molecule or lipophilic moiety further comprises the ability to tightly bind to the drag-tag. The molecules are separated in a running buffer comprising the drag-tags. The drag-tags comprise a structure having different hydrodynamic radiuses. The structure comprises a surfactant, polymer or combination thereof; as discussed above. As a consequence of the tight bonding between the molecule or lipophilic moiety and the drag-tags, the drag-tags are moved with the molecules a distance dependent upon the hydrodynamic radius of each individual drag-tag. Thus, the drag-tags would be separated by their hydrodynamic radius. Generally, drag-tags in an aqueous suspension with hydrodynamic radius between 1 nm and 1,000 nm can be assayed using the method.

Running Buffer

In some embodiments, the invention is a running buffer. The running buffer can be used in nucleic acid separation modalities or protein separation modalities. The running buffer comprises a drag-tag. The drag-tag comprises a structure selected from the group consisting of a liposome, a micelle, a solid particle, a carbon nanotube, and an oil-in-water emulsion. The structure can comprise a surfactant. The surfactant can be non-ionic, cationic, anionic, zwitterionic, or combinations thereof. Non-limiting examples of suitable non-ionic surfactants include acetylenic glycols, alkanolamides, alkanolamines, alkyl β-D-glycopyranosides, alkyl phenols, alkylglucosides, alkylmonoglucosides, fatty acids, fatty alcohols, fatty esters, glycerol esters, monododecyl ethers (such as $C_{12}E_5$, $C_{16}E_6$ and $C_{12}E_8$), phenol derivatives, poloxamers, poloxamines, polyoxyethylene acyl ethers, polyoxyethyleneglycol dodecyl ethers (such as Brij-35), sorbitols and sorbitan derivatives (such as Tween-20 and Tween-60), alkylphenol ethylene oxide condensates, alkyl ethylene oxide condensates, octylphenol ethylene oxide condensates (such as Triton X-100), fluoroalkylphenol ethylene oxide condensates, fluoroalkyl ethylene oxide condensates, partially fluorinated fluoroalkylphenol ethylene oxide condensates, partially fluorinated fluoroalkyl ethylene oxide condensates, fluorinated hydrocarbons (such as $C_8 F_{15}$, $C_{10} F_{19}$ and $C_{12} F_{23}$ and $C_6 F_{13}$), partially fluorinated hydrocarbons, fluorocarbon-based surfactants (such as Zonyl fluorosurfactants, Masurf FS-fluorosurfactants, Novec fluorosurfactants, and PEG-block-fluorocarbon copolymer fluorosurfactants), and combinations thereof. Non-limiting examples of suitable cationic surfactants include alkylamines, quaternary amines, imidazolines, dialkylamine oxides, gemini surfactants, and combinations thereof. Non-limiting examples of anionic surfactants include salts of multiple acids, salts of fatty acids, sodium dodecyl sulfates, bile acid salts, isethionates, salts of tall oil acids, alcohol phosphates, inorganic phosphates, sarcosine derivatives, alcohol sulfates, alkyl phenol sulfates, sulfated triglycerides, alpha-olefin sulfonates, linear alkylbenzene sulfonates, aromatic sulfonates, sodium alkyl sulfonates, sulfosuccinates, taurates, gemini surfactants, and combinations thereof. Non-limiting examples of zwitterionic surfactants include amino acids, betaines, imidazolines, imino acids, phospholipids, gemini surfactants, and combinations thereof. The surfactant can be at a concentration between $10^{-6}$ M and $10^{-3}$ M or with the concentration varying with time during the separation modality.

In some embodiments, the structure can comprise a polymer. Non-limiting examples of suitable polymers include polyethylene oxide (PEO) polymers, polypropylene oxide (PPO) polymers, PEO-PPO block copolymers, PEO-PPO-PEO triblock copolymers, Pluronic-type polymers, hydrophobically modified PEO polymers, protein-based polymers, polypeptides, polypeptoids, polysaccarhides, hydrophobically modified polysaccarhides, cellulose derivatives, sodium carboxymethylcellulose, hydroxymethylcellulose, hydroxyethylcellulose, hydroxypropylcellulose, hydroxypropylmethyl cellulose, alkali-soluble associative (HASE) polymers, hydrophobically modified polyacrylamides, thermally responsive polymers, N-isopropylacrylamide (NIPAAm), poly(ethylene glycol) methylether acrylate (PEGMEA), tetraethylene glycol diacrylate (TEGDA). poly(ethylene glycol)

dimethacrylate (EGDMA), N,N'-methylene-bis-acrylamide (NMBA). The polymer can be at a concentration between $10^{-6}$ and $10^{-3}$ M or with the concentration varying with time during the run.

Liposomes are formed by a variety of methods known to a person of ordinary skill. Non-limiting examples of these methods include sonication, pressure-filtration ("extrusion"), reverse-phase evaporation. A non-limiting example of liposomes suitable for use in this invention is a liposome composed of a 20:80 mixture of cholesterol and dipalmitoylphosphotidylglycerol, extruded to achieve an average size of 100 nm.

Micelles are formed by a variety of methods known to a person of ordinary skill. The micelles can be formed by adding a sufficient concentration of surfactant to reach the critical micelle concentration. At the critical micelle concentration, micelles spontaneously form. Micelles can form if the concentration of the surfactant is in the range of $10^{-6}$ and $10^{-3}$ M, depending on the surfactant in question.

The solid particles are coated with surfactants. The surfactants are applied to the solid particle by any method known to one skilled in the art. For example, a solid particle can be coated with a surfactant by liposome or vesicle fusion process where silica beads are incubated with liposomes, or by direct adsorption of surfactant and/or an associating polymer. Examples of solid particles include gold, silver, platinum, silica, titania, cadmium selenide, cadmium sulfide, indium arsenide, and indium phosphide.

The carbon nanotubes are coated with surfactants. The surfactants can be applied to the carbon nanotubes by any method known to one skilled in the art. For example, carbon nanotube bundles can be dispersed as single nanotubes by sonication in the presence of an adsorbing surfactant. These surfactants can include sodium dodecyl sulfate, sodium dodecyl benzene sulfonate, or octylphenol ethylene oxide condensate (such as Triton X-100).

Oil-in-water emulsions are formed by methods known to a person of ordinary skill in the art. They can be formed by adding the surfactant and oil to the running buffer, thereby forming a colloid. The oil-in-water emulsions can be microemulsions or nano-emulsions. For example, the emulsions can be comprised of 0.1% mineral oil in water with 0.25 mg/ml of the non-ionic surfactant C16E6 in the water phase. Such emulsions can be prepared to form particles in the size range of 40-100 nm by thermal quenching and are called "nano-emulsions."

The running buffer can further comprise a buffering system. The buffering system can be selected from the group consisting of tris(hydroxymethyl)aminomethane ("Tris") acetate, Tris HCl, Tris-2-(N-morpholino)ethanesulfonic ac (MES), phosphate buffered saline, Tris-acetate-EDTA (TAE) buffer, sodium chloride, and combination(s) thereof. In some embodiments, the running buffer further comprises 10 mM of Triton X-100 in 50 mM Tris-MES at pH 8.0.

In some embodiments, the running buffer comprises a non-ionic drag-tag. The non-ionic drag-tag can be dispersed in a liquid colloid. The non-ionic drag-tag can comprise a structure, wherein the structure is a micelle.

Phosphoramidite Synthesis of a Nucleic Acid Analog

To construct a nucleoside analog or a nucleic acid analog, a lipophilic moiety can be appended to a nucleoside or nucleic acid, for example at the 5' end of a DNA molecule, creating an alkylated nucleic acid or aDNA. The use of organic solvent systems, necessitated by the water-insolubility of the aliphatic group, is generally incompatible with the otherwise organic-insoluble oligonucleotide.

Figure 3:
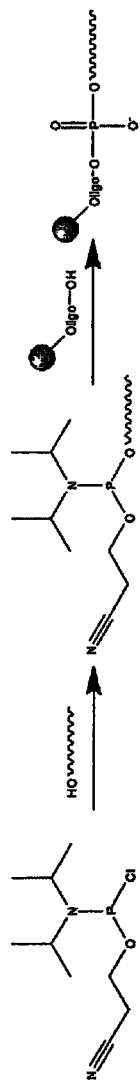
FIG. 3 is a schematic representation of the addition of a long chain alcohol to a chlorophosphoramidite and the subsequent attachment to a support bound oligonucleotide.

One example of synthesizing a hydrophobically-labeled nucleic acid is by phosphoramidite synthesis. Since oligonucleotide synthesis reactions typically take place in organic solvents, it would be ideal to perform the alkylation step on the solid support, alleviating the difficulty of finding a solvent system suitable for the coupling of the hydrophobic group. The general process behind doing so is to begin with the 2-cyanoethyl N,N' diisopropyl-chlorophosphoramidite molecule (FIG. 3). The highly reactive chloro-functional group of the phosphoramidite is substituted with a more stable long chain alcohol, for example octadecanol. This results in a $C_{18}$-labeled phosphoramidite that can later be utilized in the solid phase synthesis reaction using an automated oligonucleotide synthesizer. The phosphoramidite molecule was designed such that the aliphatic group on the final synthesized oligonucleotide would be linked through a phosphodiester bond and as a result, the phosphoramidite lacks the chemical functionality for the addition of subsequent phosphoramidites. This has the consequence that the alkylation step must be the final step in the extension of the oligonucleotide on the solid support. Since the oligonucleotide is attached to the solid support at the 3' end of the DNA molecule, the resulting aliphatic label resides at the 5' end of the synthesized oligonucleotide. Following the deprotection of the oligonucleotide and cleavage from the solid support, the aDNA oligonucleotide can be purified using reverse phase HPLC.

Example 1

The phosphoramidite synthesis method was performed as follows. 135 mg of octadecanol (0.5 mmol) was added to a round bottom flask followed by 2 ml of dry DCM (dried over molecular sieves) and sonicated to speed dissolution. 174 µl of Diisopropylethylamine (1 mmol) was added and allowed to equilibrate for 5 minutes. 112 µl of 2-cyanoethyl N,N' diisopropyl-chlorophosphoramidite (0.5 mmol) was added and the reaction was stirred at room temperature. After approximately 1 hr, the reaction was diluted with 13 ml of DCM and washed with 30 ml of saturated $NaHCO_3$. The organic layer was collected and dried over $Na_2SO_4$ and the solvent was removed by rotary evaporation. The product was purified using flash chromatography over silica gel with a hexane/ethyl acetate/triethylamine (4:1:0.05) mobile phase. The fraction containing the product, as judged by TLC, was collected and solvent was removed using a rotary evaporator. The resulting phosphoramidite was then used during the final (5') coupling during automated DNA oligonucleotide synthesis resulting in a $C_{18}$ labeled oligonucleotide.

Phosphoramidate Linkage between a Nucleic Acid and a Lipophilic Moiety

Figure 4:
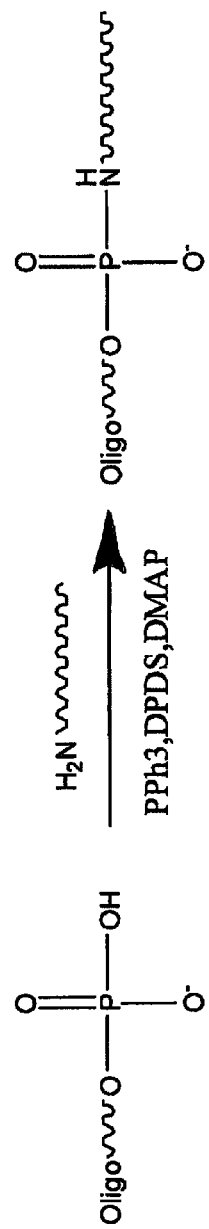
FIG. 4 is a schematic representation of a post-synthetic modification of a commercially synthesized 5' phosphorylated DNA oligonucleotide resulting in a phosphoramidate linkage between the oligonucleotide and a long chain primary amine.

Another method of alkylating a nucleic acid, illustrated in FIG. 4, is a post-synthetic modification of a 5' phosphorylated DNA oligonucleotide resulting in a phosphoramidate linkage between the oligonucleotide and a long chain primary amine. 5' phosphorylated DNA oligonucleotide is precipitated out of aqueous solution using the cationic surfactant cetyl trimethyl ammonium bromide (CTAB) and the resulting DNA-CTAB salt is readily soluble in organic solvent. This step is crucial in the success of the post-synthetic modification since, as discussed previously, the major obstacle to conventional conjugation methods is the incompatibility of the aqueous insoluble aliphatic group and the organic insoluble oligonucleotide. Upon solubilization of the DNA oligonucleotide in organic solvent, the 5' phosphate group is activated with a mixture of 2,2'-dipyridyldisulfide, triphenylphosphine and DMAP resulting in an activated terminal phosphate susceptible to nucleophilic substitution by a long chain primary amine. Following conjugation, the DNA is precipitated out of the organic solution using acetone and the oligonucleotide is purified by HPLC. The resulting linkage between the oligonucleotide and the aliphatic group is a phosphoramidate linkage.

Example 2

The phosphoramidate linkage between the oligonucleotide and a long chain primary amine was formed according to the following method. 50 µl of 2.5 mM 24 nt, 5'-phosphorylated DNA (125 nmol) in water was added to a microcentrifuge tube. The DNA was precipitated using 3 µmoles of CTAB in water (1:1 molar ratio of CTAB to phosphate groups). The resultant suspension was dried in a Speedvac and the resulting DNA/CTAB salt was resuspended in 50 µl of 0.8 M 4-(dimethylamino) pyridine (40 µmol) in DMSO dried over molecular sieves. 25 µl of 1.2 M triphenylphosphine (30 µmol) and 25 µl of 1.2 M 2,2'-dipyridyldisulfide (30 µmol) was added and allowed to equilibrate at room temperature for 15 minutes. 3 µl of TEAA (to prevent protonation of the amine) and 100 µl of 0.125 M of octadecaneamine (12.5 µmol) in DMSO at 50° C., (to promote dissolution of $C_{18}NH_2$ in DMSO) were added and the mixture was gently stirred at 50° C. for 30 minutes. The reaction mixture is precipitated with 1 ml of 2% lithium perchlorate in acetone. The suspension was centrifuged at maximal velocity (16100 g's) in a microcentrifuge and the supernatant was removed. The pellet was washed with acetone 3 times, resuspended by sonication, and centrifuged again. The supernatant was removed and the DNA oligonucleotide was suspended in 1 ml of 0.1 M TEAA buffer pH 7.0. The labeled oligonucleotide was purified using reverse phase HPLC, on a $C_{18}$ column with a 1 ml/min linear gradient from 100% TEAA to 100% acetonitrile over 30 minutes. The unmodified oligonucleotide elutes at ~11 min while the $C_{18}$ labeled oligonucleotide elutes at ~22 minutes. The individual fractions are collected and lyophilized prior to use.

Figure 8:
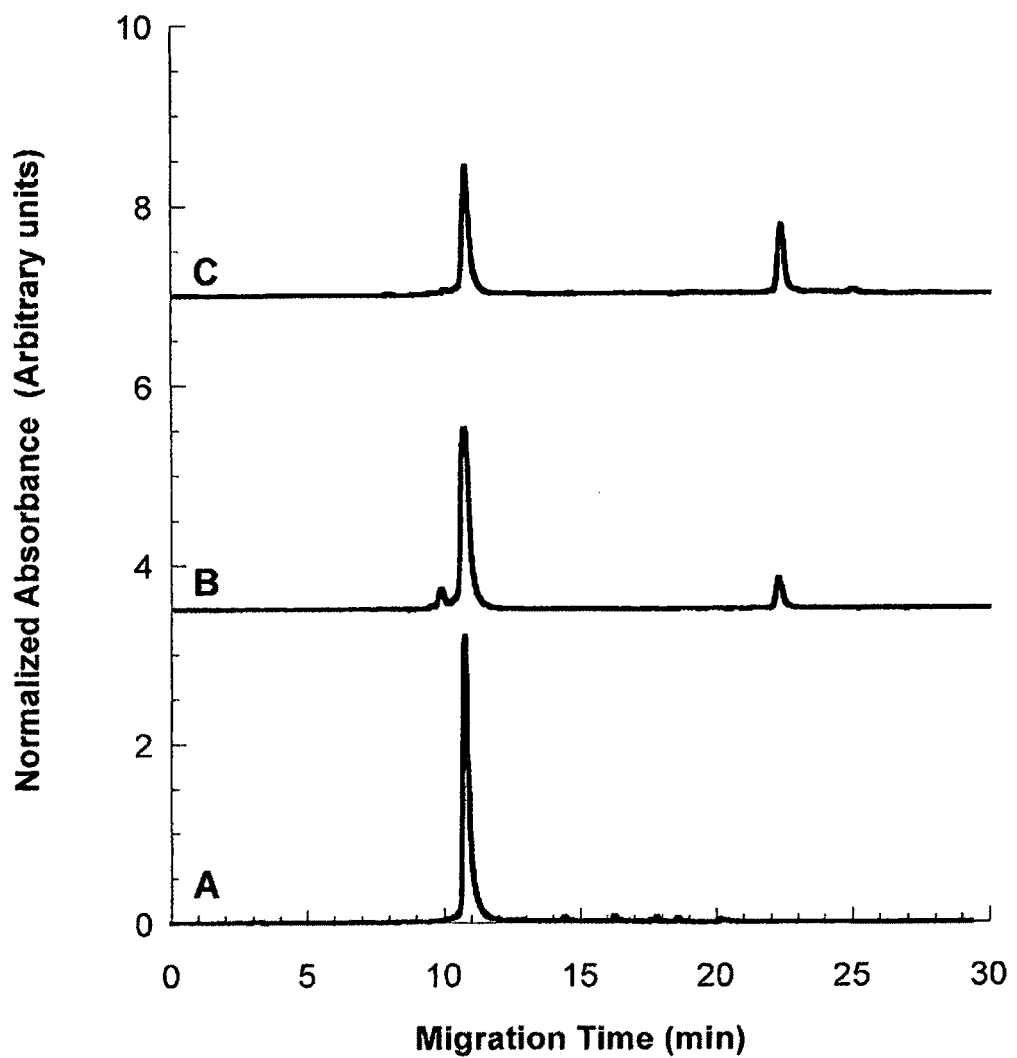
FIG. 8 is a graph illustrating data from a reverse-phase HPLC purification of $C_{18}$-aDNA conjugated through the post synthetic modification of phosphorylated DNA.

Absorbance of reverse-phase HPLC-purified $C_{18}$-aDNA confirms that the alkylation and recovery of this alkylation process was successful. The precipitation process was effective at removing the majority of conjugation reactants but any residual un-reacted DNA oligonucleotide co-precipitates with the desired aDNA. To remove the residual DNA reactant, reverse phase HPLC was conducted as with the solid-phase system above. The results of the HPLC purification are shown in FIG. 8. The chromatogram in FIG. 8(A) represents the trace corresponding to the phosphorylated DNA reactant. FIG. 8(B) is the trace from the alkylation reaction mixture following acetone precipitation in the presence of 0.1% trifluoroacetic acid. FIG. 8(C) is the trace from the same alkylation reaction in the absence of TFA. TFA is frequently added to the mobile phase in reverse-phase HPLC as an ion pairing agent to promote the interaction of positively-charged analytes with the hydrophobic media. The separation was largely devoid of positively-charged analytes, so TFA may be unnecessary here. In fact, comparing FIG. 8(B) and FIG. 8(C) demonstrates that the presence of TFA has deleterious effects on the amount of recovered alkylated DNA. The presence of TFA in the mobile phase substantially lowers the solvent's pH and that the phosphoramidate linkage between the aliphatic group and the DNA oligonucleotide appears to be labile under acidic conditions. Comparison of the peak areas in these two traces indicates that the effective coupling efficiency following purification is 11% in the presence of TFA, and 34% in its absence. In addition, subsequent analysis following successful PCR extension of the aDNA fragment recovered from FIG. 8(C) indicated a loss of hydrophobic character following repeated heating cycles, which is evidence of the fragile nature of the phosphoramidate linkage between the aliphatic group and the oligonucleotide. The lack of thermal stability of the aDNA molecule is a major concern for applications where PCR extension is desirable, but nonetheless, this method was effective in the alkylation of commercially supplied oligonucleotides and for applications at physiological pH and ambient temperatures, this method could prove useful.

Amide Linkage between a Nucleic Acid and a Lipophilic Moiety

Figure 5:
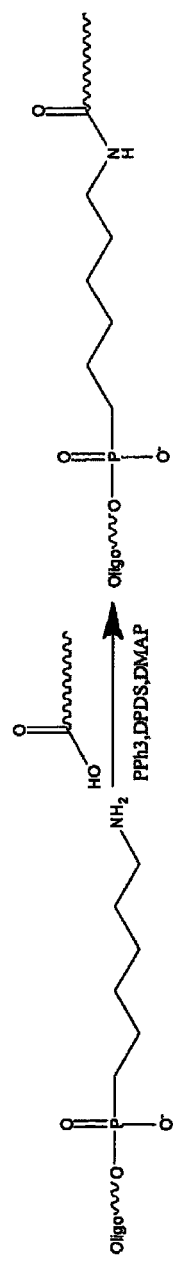
FIG. 5 is a schematic representation of a post-synthetic modification of a commercially synthesized 5' amine-labeled DNA oligonucleotide resulting in an amide linkage between the oligonucleotide and a long chain fatty acid.

Another method of alkylating a nucleoside or nucleic acid, such as a DNA, illustrated in FIG. 5, is a post-synthetic modification of a 5' amine-labeled DNA oligonucleotide resulting in an amide linkage between the oligonucleotide and a long chain fatty acid. This method uses a 5' amine-labeled oligonucleotide. A long chain fatty acid is activated with DPDS, $PPh_3$ and DMAP and mixed with the DNA-CTAB salt as before. The reaction conditions are similar to the method resulting in the phosphoramidite synthesis method; the main difference is the site of activation and the resulting linkage. In the phosphoramidite synthesis method, the phosphate group of the DNA oligonucleotide is activated while in the second method, the activation takes place on the fatty acid itself prior to incubation with the amine-labeled DNA. The linkage resulting from this approach is an amide bond and proved to be more stable under PCR thermocycling and HPLC purification conditions than the phosphoramidate bond.

Example 3

The amide linkage between the oligonucleotide and a long chain fatty acid was formed according to the following method. 5 µl of 1 M 4-(dimethylamino) pyridine (5 µmol) in DMSO dried over molecular sieves, was added to a 1.5 ml centrifuge tube containing 20 µl of 5 mM fatty acid or Bodipy fatty acid analog (100 nmol) and 1 µA triethylamine. 5 µl of 0.5 M triphenylphosphine (2.5 µmol) and 5 µl of 0.5 M 2,2'-dipyridyldisulfide (2.5 pimp was added and allowed to equilibrate at room temperature for 5 minutes. Meanwhile, 10 nmol of 24 nt, 5' amino-modified DNA (Integrated DNA Technologies, Coralville, Iowa) in water was added to a centrifuge tube. The DNA was precipitated by adding 230 nmol of CTAB in water (1:1 molar ratio of CTAB to phosphate groups). The suspension was dried by vacuum centrifugation and the resulting DNA/CTAB salt was resuspended in the reaction mixture, and allowed to react with vigorous agitation for 2 hours. The reaction mixture was precipitated with 1 ml of 2% lithium perchlorate in acetone. The suspension was centrifuged at maximum velocity (16100 g's) in a microcentrifuge and the supernatant is removed. The pellet was washed with acetone 3 times, resuspended by sonication, and centrifuged again. The supernatant was removed again and the DNA oligonucleotide was suspended in 25 µl of 0.1 M triethylammoniumacetate buffer pH 7.0. The labeled oligonucleotide was purified using reverse phase HPLC, on a $C_{18}$ column with a 1 ml/min linear gradient from 100% TEAA to 100% acetonitrile over 60 minutes. The unmodified oligonucleotide eluted at ~17 minutes while the alkylated DNA oligonucleotide eluted at ~31 minutes. The individual fractions were collected and dried, either through lyophilization or vacuum centrifugation prior to use.

Figure 9:
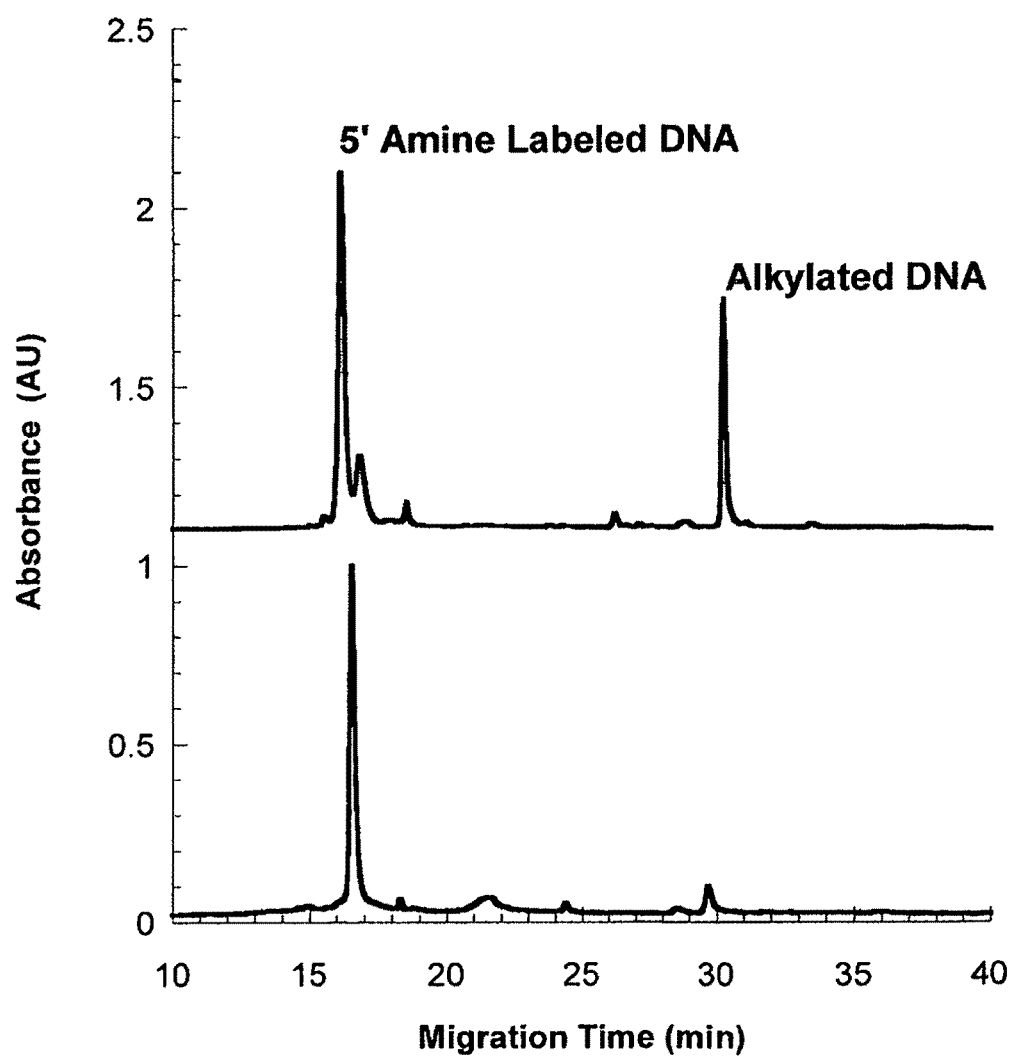
FIG. 9 is a graph illustrating data from a reverse-phase HPLC purification of $C_{12}$-Bodipy-Fl aDNA conjugated through the amide bond formation method.

Absorbance of reverse-phase HPLC-purified $C_{18}$-aDNA confirms that the alkylation and recovery of this alkylation process was successful. The DNA oligonucleotide was precipitated out of aqueous solution with the cationic surfactant CTAB, so that it would be compatible with the organic solvent system required for the dissolution of the fatty acid aliphatic group. The results from HPLC purification from this reaction method can be found in FIG. 9. This particular purification is of a 24-base oligonucleotide conjugated to the hydrophobic $C_{12}$-Bodipy-Fl fluorophore. As before, FIG. 9(A) represents the chromatogram of the $C_{12}$-Bodipy-Fl fatty acid. The small peak at 30 minutes was an impurity that was injected with the fatty acid control and did not affect the subsequent purification of the aDNA, represented in FIG. 9(B). Comparison of peak areas indicated a coupling efficiency of 27%. There is a small population evident immediately after the unlabeled DNA reactant that has the characteristic UV spectrum of a nucleic acid. This may be a side product of the conjugation reaction itself. Since it elutes at a migration time markedly different from the alkylated DNA, it is of little consequence for the purification of the aDNA. The presence of TFA in the mobile phase did not seem to impact the efficiency of the coupling nor did prolonged exposure to elevated temperature, a result of the substantially more stable amide linkage between the aliphatic group and the oligonucleotide.

These methods rely on the precipitation of DNA from aqueous solution followed by suspension of the resulting DNA/CTAB salt in DMSO. Once the DNA was solubilized within the organic solvent system, activation of the terminal phosphate with DPDS, $PPh_3$ and DMAP permitted the covalent attachment of various long-chain carboxylic acids to the oligonucleotide. Following the conjugation reaction, the alkylated DNA was precipitated out of DMSO using acetone and $LiClO_4$.

Example 4

In order for a separation modality to be capable of performing separations of DNA sequencing products, the physical mechanism responsible for the separation must be compatible with the extension of the primer by DNA polymerase. Since the enzymes typically used for DNA sequencing are minor mutations of enzymes commonly employed in PCR, the ability of PCR enzymes to extend aDNA primers translated well to DNA sequencing applications. Tests using a nucleic acid primer comprising a lipophilic moiety bonded to the 5' end confirmed that the alkylation of the nucleic acid does not inhibit DNA polymerase from extending the primer, or the primer annealing to the template.

UV melting curves were used to determine the melting temperature of the alkylated DNA generated using solid phase synthesis. UV melts were conducted in a Varian Cary 3 spectrophotometer bearing a peltier controlled cell holder. The 34 nt synthetic aDNA oligonucleotide was incubated with its commercially-synthesized 34 nt complement at a final concentration of 1 µM each in 50 mM Tris MES, pH 8.0. The sample was heated to 95° C. and held for 5 minutes to ensure complete denaturation of the two strands. The temperature was then lowered to 15° C. at a rate of 1° C./min while the absorbance was read at 260 nm. The sample was held at 15° C. for 5 minutes prior to a 1° C./min heating cycle back to 95° C.

Sanger-type cycle sequencing reactions were performed to confirm that alkylated DNA primers are compatible with this method, commonly used for the generation of extension products for DNA sequencing purposes. The reactions were conducted in a SmartCycler (Cepheid, Sunnyvale, Calif.) at a total volume of 20 µl. Cycle sequencing reactions based on the Therminator DNA polymerase included the following: 1000 nM $C_{12}$ Bodipy-Fl-aDNA or $C_{18}$-aDNA primer, 0.05 mM dNTP mixture 0.1 mM chain terminator (acyATP or Fluorescein-labeled ddGTP), 1× Thermo Pol buffer, (New England Biolabs, Ipswich, Mass.), 100 ng/µl M13 mp18 single-stranded DNA template, (NEB), and 0.05 Units/µl Therminator DNA polymerase (NEB). The thermocycling conditions were as follows: An initial template denaturation step of 5 minutes at 95° C. was conducted, followed by 55 cycles of 95° C. for 30 seconds, 55° C. for 30 seconds, and 72° C. for 120 seconds. A final elongation step following thermal cycling was conducted for 5 minutes at 72° C. Following reaction, residual nucleotide triphosphates and reaction buffer salts were removed using a Centri-Sep column. (Princeton Separations, Princeton, N.J.). The resulting purification product was either mixed with 2×TBE-Urea loading buffer (Promega) prior to denaturing polyacrylamide gel electrophoresis, or loaded into the capillary electrophoresis in distilled water.

Extension success was measured by polyacrylamide gel electrophoresis (PAGE). Polyacrylamide gels were prepared by combining 40% acrylamide/bis acrylamide (37.5:1) solution (BioRad Laboratories, Hercules, Calif.) in 10×TBE buffer (89 mM Tris base, 89 mM Boric acid, 20 mM EDTA pH 8.3) and DI water. The mixture was vortexed briefly and degassed in a vacuum chamber for 15 minutes. Following degassing, N,N,N',N'-Tetramethylethylenediamine and ammonium persulfate were added to final concentrations of 0.5% v/v and 0.01% w/v respectively. Typically, gels were cast to a final acrylamide concentration of 5% into 1 mM thick, 7.3 cm tall, 8 mM wide gels. Cast gels were loaded into a Mini-Protean 3 vertical electrophoresis chamber (BioRad Labs) and a mixture of the DNA to be analyzed and 6× loading dye (Promega) in water were loaded into the gel. A voltage of 150-200 V was applied (E≈20-27 V/cm) and typical run times were approximately 45 minutes. Following electrophoresis, the gel was stained with Ethidium Bromide and visualized with a BioDocIt transilluminator (UVP, Upland, Calif.). The lengths of the fragments in the ladder, in bp, are in the column on the left. The contents of each of the 9 lanes are as follows: 1) PCR marker ladder, 2) 107 bp unlabeled DNA, 3) 107 bp $C_{12}$-Bodipy-Fl labeled aDNA, 4) 107 bp unlabeled DNA, 5) 107 bp $C_{12}$-Bodipy-Fl labeled aDNA, 6) 255 bp unlabeled DNA, 7) 255 bp $C_{12}$-Bodipy-Fl labeled aDNA, 8) 450 bp unlabeled DNA, 9) 450 bp $C_{12}$-Bodipy-Fl labeled aDNA. Staining was conducted with ethidium bromide (FIG. 10).

Figure 10:
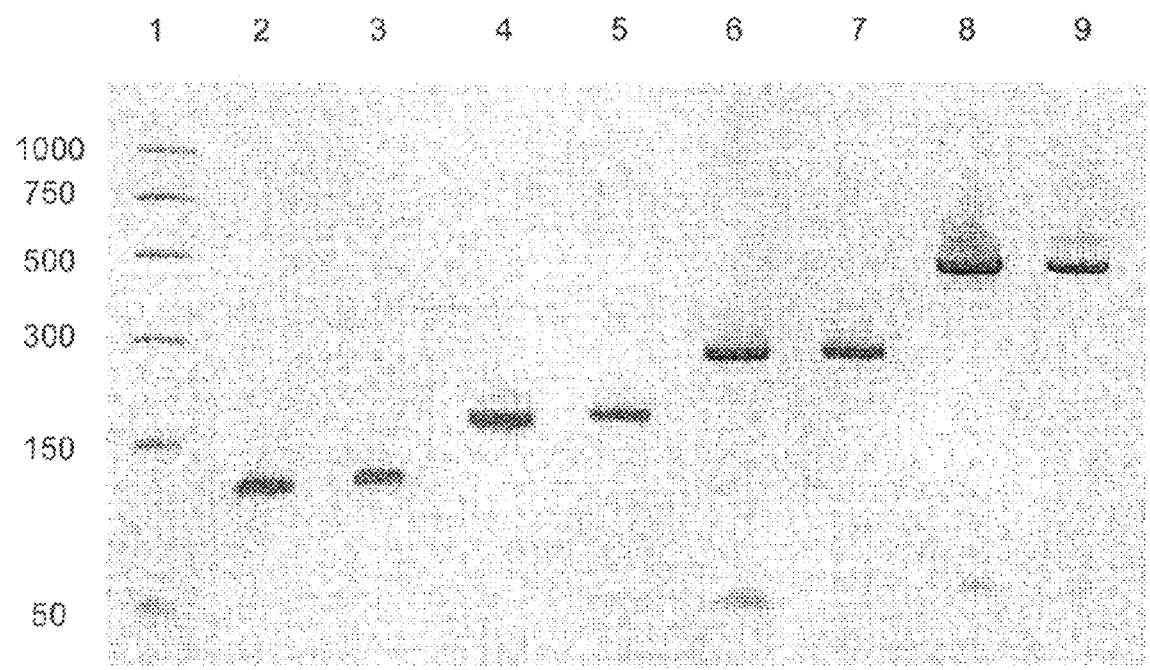
FIG. 10 is an image of a 5% polyacrylamide gel electrophoresis of alkylated and non-alkylated PCR primer products for 4 different extension product lengths.
Figure 11:
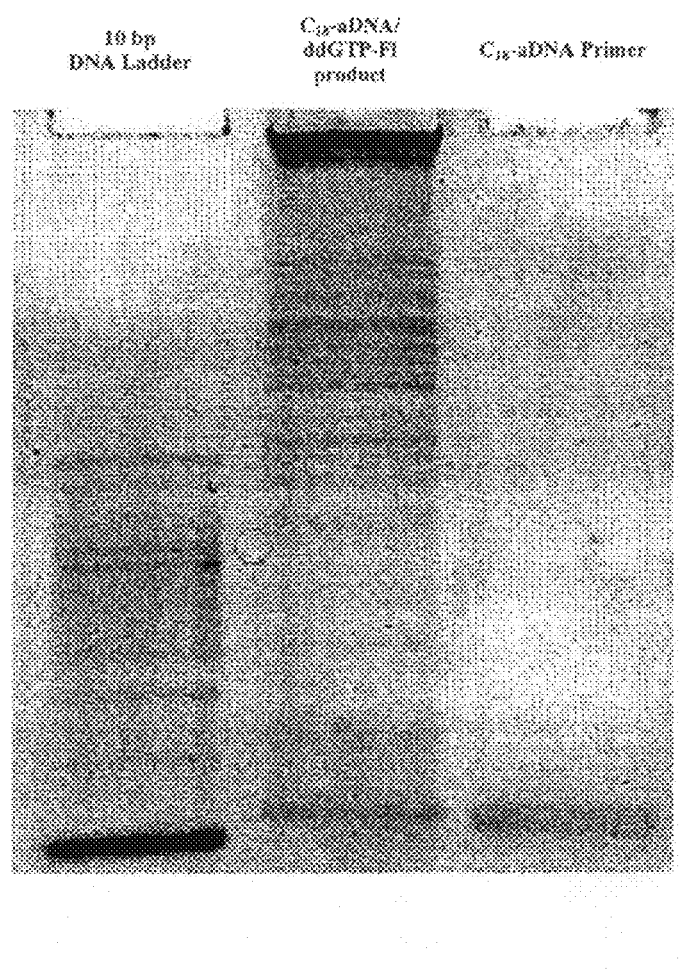
FIG. 11 is an image of a denaturing polyacrylamide gel electrophoresis of $C_{18}$-aDNA sequencing product resulting from fluorescein-labeled-ddGTP chain terminator extended by Therminator DNA polymerase.

The gels confirmed that the alkylated nucleic acid primers were extended successfully (see FIG. 10). The first and most important feature of this figure is that the addition of a hydrophobic group, (a $C_{12}$-Bodipy fatty acid tail) does not appreciably hinder the polymerase's ability to extend the labeled primer. There is approximately a 20% reduction in the band intensity for each of the alkylated PCR products as judged by subsequent densitometric scans, indicating a slight extension bias against the labeled primer. The PCR reaction was equally specific for the labeled primer and the resultant band intensities are indicative of a substantial degree of primer amplification.

Another important feature present in the above gel is the slight shift between labeled and unlabeled PCR fragments. This is more prevalent for the shortest PCR products, specifically the 107 bp product found in lanes 2 and 3. This is to be expected, owing to the fact that the electrophoretic mobility shift induced by the aliphatic tail will have diminishing impact on increasing lengths of DNA targets. This shift could be explained by an increased hydrodynamic drag relevant to the naked DNA itself, following a mechanism analogous to the ELFSE-based drag in free solution. Namely, the tail is able to break the charge-to-friction ratio of the DNA fragment while it is migrating through the pores of the polyacrylamide.

The drag associated with the relatively small lipophilic moiety would not be substantial enough to induce an appreciable shift for long PCR products, consistent with the above observation that there is only a detectable shift for the shortest two product lengths. Secondly, since the polyacrylamide gel matrix possesses a moderate degree of hydrophobic character, the tag could be transiently associating with the matrix itself. Since the matrix is stationary, any favorable interactions that the PCR fragment has with the gel matrix would retard the migration of the fragment, even if the interactions are weak. This would be analogous to the drag induced by a drag-tag with an infinite a, and any length dependence of the electrophoretic mobility shift caused by the hydrophobic group must be a result of differential interaction with the stationary gel matrix. It is unknown which of these two factors would dominate but since the focus of this work is aimed at the separation of DNA fragments in the absence of a polymer matrix, it will simply be left as a curiosity. It does, however, suggest a new separation modality, namely that while conducting a gel electrophoresis experiment, micelles could be added to the running buffer to induce an even greater electrophoretic mobility shift of the alkylated PCR fragments.

Although three successful methods were established for DNA alkylation, the post-synthetic modification of a 5' amine labeled DNA with a long chain fatty acid presented the greatest degree of sequence reliability, ease of conjugation and alkylation stability. The characterization of the conjugation involved ascertaining the degree of hydrophobicity conferred through the alkylation in reverse-phase HPLC and the subsequent extension of the alkylated primer in PCR.

Cycle sequencing reactions for sequencing analysis on the ABI 310 Genetic Analyzer were based on the BigDye cycle sequencing reaction kit, version 3.1. The reaction mixture included the following: 1000 nM $C_{18}$ aDNA primer, 100 ng/µl M13mp18 single-stranded DNA template, (NEB), 6 µl of 2.5× sequencing buffer (200 mM Tris HCl pH 9.0+5 mM $MgCl_2$) and 2 µl of the BigDye v 3.1 reaction mixture (Applied Biosystems). The thermocycling conditions were as follows. An initial template denaturation step of 5 minutes at 95° C. was conducted, followed by 55 cycles of 95° C. for 30 seconds, 55° C. for 30 seconds, and 72° C. for 240 seconds. A final elongation step following thermal cycling was conducted for 5 minutes at 72° C. Following reaction, residual nucleotide triphosphates and reaction buffer salts were removed using a Centri-Sep column (Princeton Separations, Princeton, N.J.). The resulting purification product was dried by vacuum centrifugation and reconstituted in HiDi Formamide (Applied Biosystems).

The Therminator DNA polymerase was used to extend the $C_{18}$ primer in a sequence dependent fashion along the single-stranded M13mp18 DNA template. Termination of sequencing fragments was accomplished through the use of a fluorescein-labeled ddGTP (ddGTP-Fl) chain terminator. As a first pass, the generation of sequencing fragments from a single chain terminator was investigated for proof-of-principle experiments in MEKC.

Figure 13:
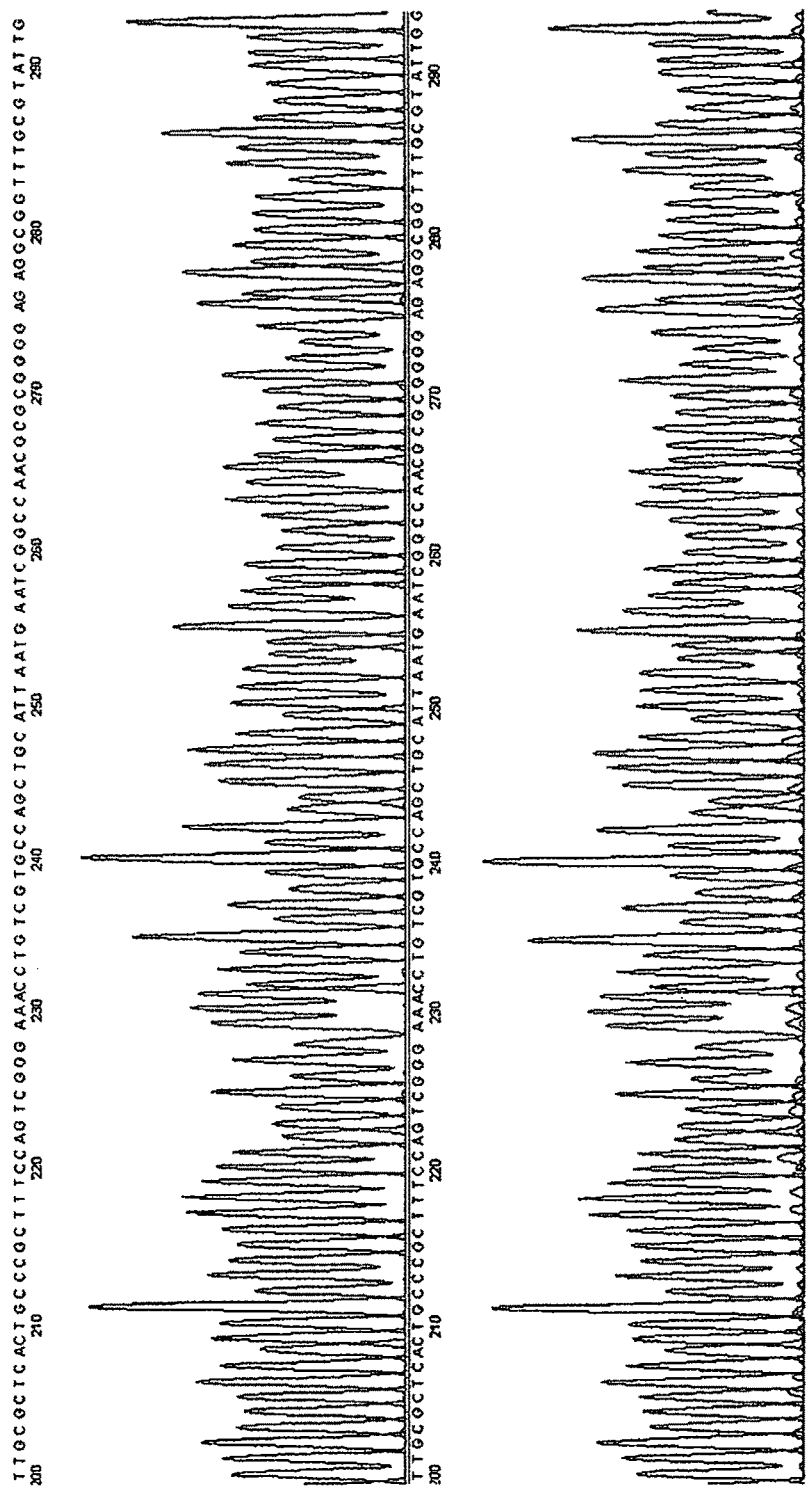
FIG. 13 illustrates a comparison of the sequences determined for the unlabeled (upper trace) and $C_{18}$-labeled (lower trace) DNA primer.

To confirm the successful generation DNA sequencing fragments, the cycle sequencing reaction was separated using denaturing polyacrylamide gel electrophoresis. The results of this separation may be found in FIG. 13. The left most lane represents the migration behavior of a 10 bp DNA ladder. This particular ladder is composed of double-stranded DNA fragments in increments of 10 bp from 20 to 100 bp in length. It is clear that there is not a uniform spacing between the 10-base fragments generated through the denaturation process prior to introduction to the gel. Additionally, there appear to be more than 10 bands present in the lane. This is most likely explained by differing migration of the individual strands of the double-stranded fragments once they are denatured. The lowest band in the lane is the 20-base fragment and the uppermost band corresponds to a molecular weight of 100 bases. This provides a qualitative indication of the relative lengths of DNA bands that are electrophoresing in other lanes. The $C_{18}$-primer may be found at the far right of the gel, and was loaded at an identical concentration to the $C_{18}$ primer in the cycle sequencing reaction. The center lane represents the results from the cycle sequencing reaction itself. Although the resolution of bands is poor, there are certainly a significant number of sequencing fragments present in the mixture. This particular gel is not expected to successfully resolve sequencing fragments longer than 20-25 bases. This is due to the small size of the gel itself. This particular gel is just over 7 cm long and in order to achieve adequate separation between fragments, this experiment would have to be repeated on a substantially larger sequencing gel 40 to 50 cm in length. Nonetheless there is still adequate evidence of the successful generation of distinct sequencing fragments. Closer inspection of the dark band immediately below the wells indicates the presence of two different populations. These two populations represent residual template, which is ~7200 bases long, and the full length extension product expected to be ~6300 bases. It is difficult to ascertain the relative amounts of each of the populations present within the gel. One of the major complications prohibiting quantification, in addition to inadequate resolution, is the fact that increasingly longer DNA fragments take up an increasing amount of the stain used for visualization. Also, the presence of faint bands latitudinal across the entire gel is evidence of inadequate filtering of infrared light generated by the transilluminator. The major purpose of this experiment was the confirmation of the ability to produce a mixture of DNA fragments of varying lengths from the extension of the aDNA sequencing primer and this particular gel is evidence of this.

Example 5

DNA fragments were prepared by a PCR reaction. Cycle sequencing reactions were conducted in a SmartCycler (Cepheid, Sunnyvale, Calif.) at a total volume of 20 µl. Cycle sequencing reactions based on the Therminator DNA polymerase included the following: 1000 nM $C_{12}$ Bodipy-Fl-aDNA or $C_{18}$-aDNA primer, 0.05 mM dNTP mixture 0.1 mM chain terminator (acyATP or Fluorescein-labeled ddGTP), 1× Thermo Pol buffer, (New England Biolabs, Ipswich, Mass.), 100 ng/µl M13mp18 single-stranded DNA template, (NEB), and 0.05 Units/µl Therminator DNA polymerase (NEB). The thermocycling conditions were as follows: An initial template denaturation step of 5 minutes at 95° C. was conducted, followed by 55 cycles of 95° C. for 30 seconds, 55° C. for 30 seconds, and 72° C. for 120 seconds. A final elongation step following thermal cycling was conducted for 5 minutes at 72° C. Following reaction, residual nucleotide triphosphates and reaction buffer salts were removed using a Centri-Sep column. (Princeton Separations, Princeton, N.J.). The resulting purification product was either mixed with 2×TBE-Urea loading buffer (Promega) prior to denaturing polyacrylamide gel electrophoresis, or loaded into the capillary electrophoresis in distilled water.

Prior to the separation of DNA sequencing fragments according to the invention, it was necessary to determine whether the alkylation of the DNA primer had a significant impact on the extension ability of the polymerase typically used in conjunction with the instrument. This was performed on an ABI Prism 310 Genetic Analyzer, (Applied Biosystems, Foster City, Calif.). The capillary used was a 50 µm I.D. fused silica capillary (Polymicro Technologies, Phoenix, Ariz.), 61 cm total length, 50 cm length to detector and maintained at a temperature of 50° C. The sieving matrix employed was POP6 polymer (Applied Biosystems). Electrokinetic injection (2.5 kV for 30 seconds) was used to introduce the DNA sequencing fragment mixture into the capillary. Electrophoretic separation was conducted under reverse polarity (from cathode to anode) with an electric field strength of 200 V/cm.

The ABI Prism 310 Genetic Analyzer is a four-color, capillary gel electrophoresis-based DNA sequencing instrument. The specific benefit of a four-color instrument is that the sequencing fragments can be separated simultaneously. This is done through the use of chain terminators that are each labeled with a different fluorophore. As a result, the particular identity of the terminal base of a fragment is specific to a unique fluorophore and provided the detector signal can be spectrally filtered properly, the simultaneous detection of each of the four terminators is possible. Another key feature of the chain terminators commonly used by the ABI 310, BigDye terminators, is the fact that they are all excited with the same laser light. The dyes attached to the chain terminators are not simply a single fluorophore, but rather a pair of FRET-coupled fluorophores separated by a short flexible liker. Each of the FRET pairs share a common donor fluorophore but the acceptor fluorophore it is attached to is unique for each of the four chain terminators. As a result, each terminator can be excited by laser light at 488 nm, but they emit light at varying wavelengths, from ~520 to ~625 nm. The instrument's detector is essentially a color CCD, and "virtual" filters within the software filter out any bleed-through between different channels. In an effort to determine the compatibility of aDNA sequencing primers with the chain terminators and enzymes used by the instrument, a cycle sequencing reaction was performed with two different sequencing primers. The two primers shared an identical length and sequence, only differing in the attachment of a $C_{18}$ aliphatic group, and were each used to sequence the M13mp18 ssDNA template. Following the cycle sequencing reaction, the samples were purified to remove residual BigDye terminators and subsequently separated by CGE using the POP6 polymer designed for DNA sequencing applications.

Analysis of BigDye-terminated sequencing fragments was conducted by capillary gel electrophoresis. The capillary used was a 50 µm I.D. fused silica capillary (Polymicro Technologies, Phoenix, Ariz.), 61 cm total length, 50 cm length to detector and was maintained at a temperature of 50° C. 0.1% w/v POP6 polymer (Applied Biosystems) was used to suppress EOF. Under these conditions, POP6 was seen to reduce the magnitude of EOF from $4.5 \times 10^{-4}$ to $0.08 \times 10^{-4}$ cm$^2$/Vs. Electrokinetic injection (2.5 kV for 30 seconds) was used to introduce the DNA sequencing fragment mixture into the capillary. Electrophoretic separation was conducted under reverse polarity (from cathode to anode) with an electric field strength of 200 V/cm. Typical analysis time was 2 hours.

Analysis of Terminator enzyme-extended sequencing products was performed on a P/ACE MDQ (Beckman Coulter, Fullerton, Calif.) equipped with a laser induced fluorescence, or LIF, detector. Data collection and analysis was performed using 32 Karat software (Beckman Coulter). The capillary used was a 50 µm I.D. fused silica capillary (Polymicro Technologies, Phoenix, Ariz.), 31 cm total length, 21 cm length to detector.

Hydrodynamic injection (0.5 psi for 5 seconds) was used to introduce sample into the capillary. Electrophoretic separation was conducted under normal polarity (from anode to cathode) with an electric field strength of 700 V/cm. LIF detection of the $C_{16}$-Bodipy-F1 labeled sequencing fragments was performed with excitation/emission wavelengths of 488/520 nm. The capillary coolant temperature was maintained at 22° C. and samples were stored at 10° C. in DI water prior to injection.

Figure 15:
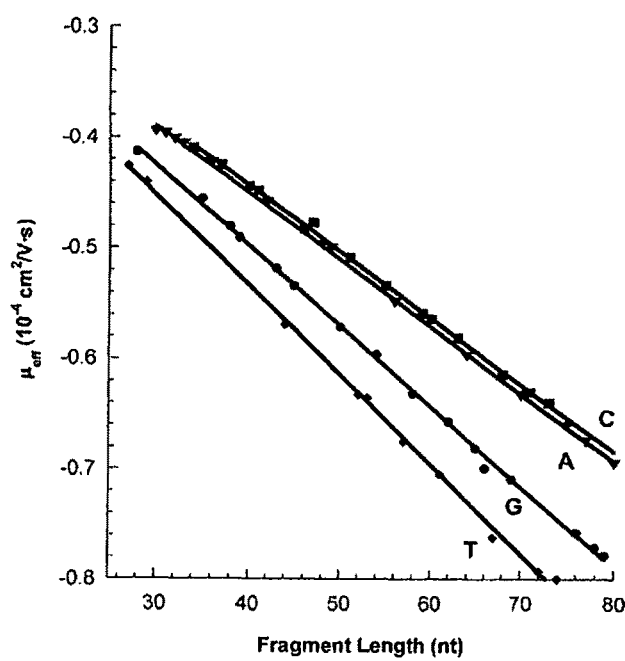
FIG. 15 is a graph illustrating the effective mobilities of $C_{18}$-aDNA sequencing fragments 28-80 bases in length.

Following the electrophoretic separation, the sequencing analysis software spectrally filtered the raw data, and employed a base calling algorithm to determine the sequence of the DNA templates used in the two preparations. An abbreviated portion of the sequencing traces, including the called bases for each trace, can be found in FIG. 15. The lower curve represents the called bases from base 200 to base 300 for the $C_{18}$-cDNA, the upper curve representing the unlabeled fDNA. Not only were the called bases over this entire region identical, the peak shapes and peak intensities were virtually identical between the two samples, indicating no termination bias between the unlabeled and the $C_{18}$-labeled sequencing primers. In addition to the 100-base region depicted in FIG. 15 the two sequences were 99% homologous over a 600 base stretch, deviating by only 2 called bases.

Example 6

In the experiment to test separating DNA by transiently attaching a drag-tag to an allylated DNA analog, a running buffer comprises a drag-tag having a micelle structure was used. The micelle was formed with Triton X-100 from Fluka. Stock solutions of Triton X-100 were prepared by vortexing a suitable amount of Triton in 50 mM Tris MES buffer, pH 8.0, to arrive at a stock concentration of 48 mM. Aliquots were prepared at concentrations ranging from 1.2 to 48 mM, vortexed, and centrifuged to remove bubbles. The Tris MES buffering system was chosen in an effort to minimize fronting of the DNA peak caused by electrodispersion. Tris HCl and Tris acetate buffering systems were also investigated but produced significant peak distortion for high DNA concentrations. Notwithstanding this distortion, Tris HCl and Tris acetate may be used as alternative buffering systems, although Tris MES is preferred.

Example 7

Following successful sequencing of the M13mp18 template with an alkylated DNA primer using capillary gel electrophoresis, the alkylated DNA primer was used to synthesize an alkylated DNA analog for use in a separation modality while transiently attaching drag-tags to the alkylated DNA analog. Specifically, the DNA analogs were separated by free-solution electrophoretic in the presence of non-ionic Triton X-100 micelles.

Figure 12:
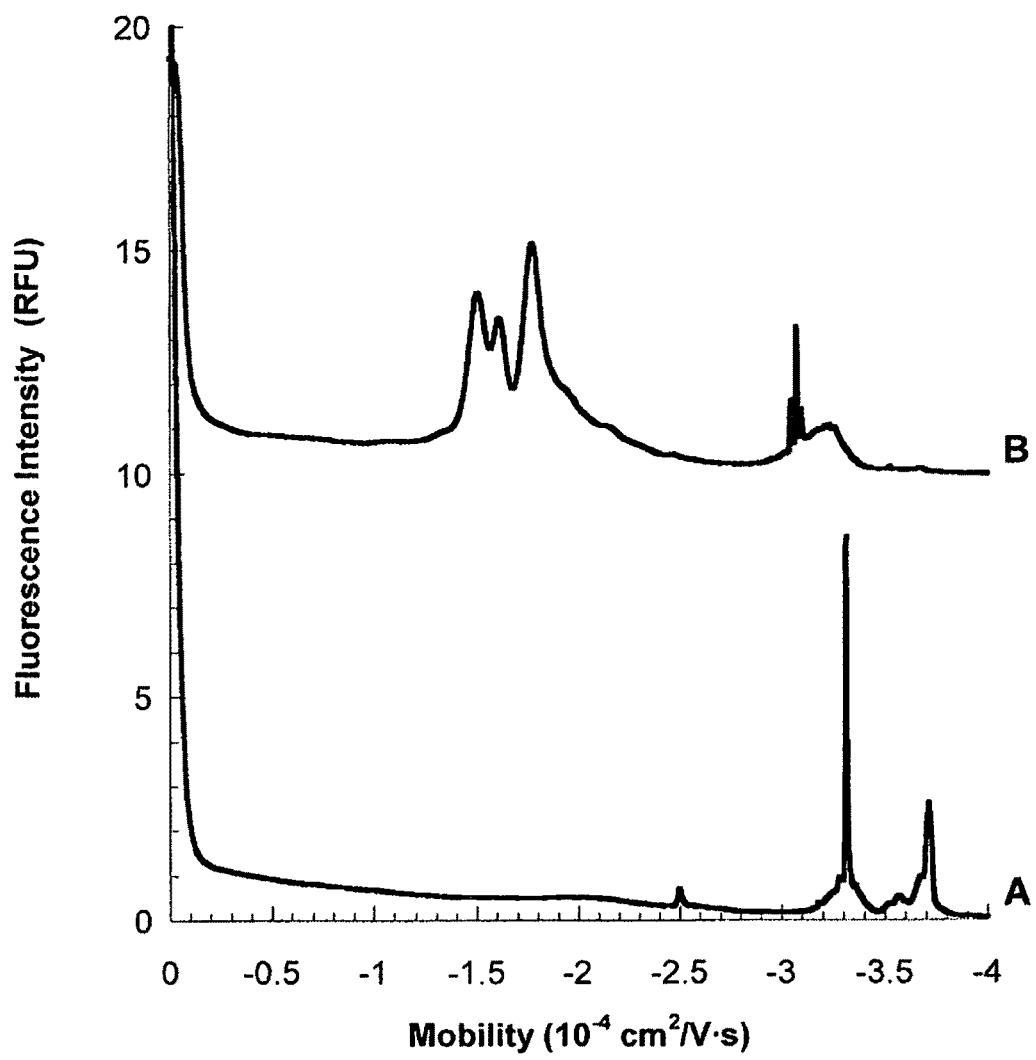
FIG. 12 is an electropherogram of $C_{12}$-Bodipy-Fl-aDNA sequencing terminated by acyATP with Therminator DNA polymerase.

The molecule, a DNA analog, was synthesized by PCR. The primer used in the PCR reaction was a $C_{12}$-Bodipy-F1-aDNA primer, and the reaction was carried-out in the presence of acyclic-ATP chain terminators. Acyclic nucleotide triphosphates are nucleotide analogs that lack the cyclic sugar group of a standard deoxyribonucleotide. As a result, they lack the 3' OH functionality required for elongation by polymerase enzymes. This particular chain terminator was selected due to its well documented incorporation kinetics with the Therminator enzyme but, provided the dNTP/chain terminator ratio is chosen appropriately, the results of most chain terminator chemistries are expected to be comparable. Following the sequencing reaction, the samples were desalted and resuspended in distilled water prior to injection in the capillary electrophoresis instrument. The results of the separation can be seen in FIG. 12. The two sequences deviated by only 2 called bases for over 600 bases (99% Homologous).

The lowest electropherogram, FIG. 12(A), represents the separation of the sequencing fragment in the surfactant-free running buffer. The tallest peak is expected to correspond to single-stranded DNA, most likely the primer. The second population at $3.8 \times 10^{-4}$ cm$^{-2}$/Vs corresponds to double-stranded DNA resulting from various sequencing fragments hybridized to the M13mp18 template.

The addition of 48 mM Triton X-100 to the running buffer, FIG. 12(B), demonstrates the successful alkylation of sequencing fragments of various lengths. The broad peak at approximately $-3.2 \times 10^{-4}$ cm$^2$/Vs represents the double-stranded DNA. More importantly however, this electropherogram demonstrates the presence of multiple peaks, presumed to be single-stranded in nature, that show a significant degree of interaction with the micellular phase. These are the fragments between $-1.5$ and $-2.5 \times 10^{-4}$ cm$^2$/Vs. Thus, it is clear that the cycle sequencing reaction is producing fragments of different lengths, and the presence of micelles in the running buffer impacts the electrophoretic mobility of these fragments.

Additionally, the magnitude of the peaks for larger fractions is quite small. This is most likely a result of the fact that this particular instrument is not specifically designed for the extremely low fluorescent signals generated from these sequencing fragments. As a result, a capillary electrophoretic system designed specifically for DNA sequencing applications was used to investigate the use of micelles for the separation of sequencing fragments.

Although data collection followed a protocol identical to that of the capillary gel electrophoresis sequencing separation, the non-standard peak spacing rendered it difficult for the current version of the sequence analysis software to accurately identify the bases. The base caller employed by the analysis software requires near constant peak spacing to accurately determine the sequence of basis separated. The migration time of a DNA fragment of length $L_{DNA}$ is given by $$t(L_{DNA}) = \frac{1_D 1_t}{V \mu(L_{DNA})} = \frac{1_D 1_t}{V \mu_o} \left( \frac{L_{DNA} + \alpha}{L_{DNA}} \right) = \frac{1_D 1_t}{V \mu_o} \left( 1 + \frac{\alpha}{L_{DNA}} \right).$$

Rather than 1 increasing linearly with $L_{DNA}$, t scales as $1/L_{DNA}$. As a consequence, the processing of the electropherogram must be done manually. The first and most important step in the processing of the raw intensity vs. time data is to spectrally filter the signals as discussed previously. To do this, the matrix file associated with the dye, in this case, the BigDye v3.1 matrix, was used. The matrix file represents a matrix of values that indicate the normalized intensity of each of the four dyes (the columns of the matrix) in each of the four virtual filters (the rows of the matrix) and is stored in the instruments software. The matrix used for this particular data set was:

$$\text{Matrix} = \begin{bmatrix} 1.00 & 0.23 & 0.01 & 0.01 \\ 0.40 & 1.00 & 0.15 & 0.00 \\ 0.24 & 0.49 & 1.00 & 0.28 \\ 0.07 & 0.24 & 0.44 & 1.00 \end{bmatrix}$$

Here, the diagonal elements of the matrix are equal to 1. This is equivalent to stating that the normalized intensity of the blue dye measured in the blue filter for example, is equal to 1. Also, as one moves away from the diagonal, the normalized intensities decrease. This is equivalent to saying that the normalized intensity of blue dye measured in the green channel (0.23) would be higher than the intensity of the blue dye measured in the yellow channel (0.01). Once the matrix is known, each of the four channels of raw data can be normalized for the contribution of its total intensity from each of the four channels, eliminating spectral overlap from the data. Mathematically speaking, this process is equivalent to:

$$[\text{Filtered Data}] = \begin{bmatrix} 1.00 & 0.23 & 0.01 & 0.01 \\ 0.40 & 1.00 & 0.15 & 0.00 \\ 0.24 & 0.49 & 1.00 & 0.28 \\ 0.07 & 0.24 & 0.44 & 1.00 \end{bmatrix}^{-1} \times \begin{bmatrix} \text{blue data} & \rightarrow \\ \text{green data} & \rightarrow \\ \text{yellow data} & \rightarrow \\ \text{red data} & \rightarrow \end{bmatrix}$$

Following spectral deconvolution, the data is passed through a moving median filter to eliminate noise in the electropherogram and finally a unique constant intensity is subtracted from each of the channels bringing the baseline of each to a value of 0. After the fluorescence intensity is normalized, the migration time axis can be converted to allow comparison with measurements discussed previously. This is accomplished by applying the following equation $$\mu_{app} = \frac{1_D 1_T}{Vt}.$$

Figure 14:
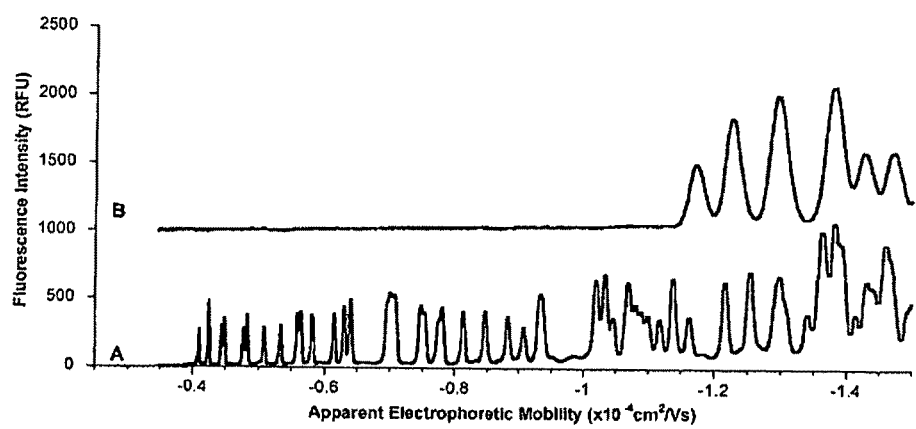
FIG. 14 is an electropherogram from the "C" channel of a free solution electrophoretic separation in 48 mM Triton X-100 of A) $C_{18}$-aDNA sequencing primer, B) unlabeled DNA sequencing primer.
Figure 16:
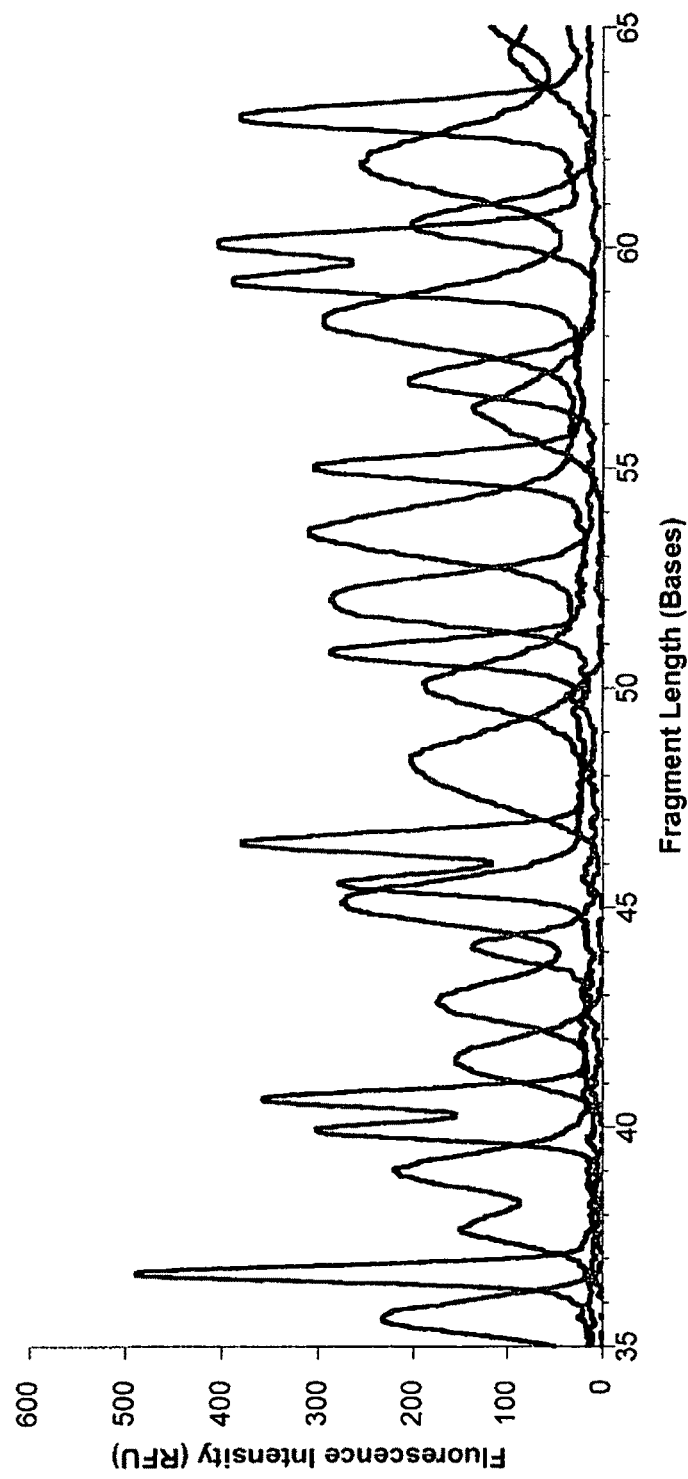
FIG. 16 is a graph illustrating data from sequencing of M13 mp18 ssDNA template with a $C_{18}$-aDNA primer ($C_{18}$-M13 (−47)).

The result of the normalization procedure has been shown in FIG. 16. This particular set of electropherograms is the result of a micellular-aDNA interaction during separation for the same set of sequencing primer investigated sequenced via capillary gel electrophoresis, discussed above. Only the "C" channel has been displayed for clarity. In FIG. 14(A), the addition of the aliphatic tail is shown to have a profound impact on the measured electrophoretic mobility.

Not only are there a substantial number of generated fragments, but there is significant resolution between a large number of the populations generated. The electrophoretic mobility of the smallest fragment is approximately $-0.4 \times 10^{-4}$ cm$^2$/Vs. This is substantially lower than the value expected for even the shortest length possible within the mixture, 25 bases. The experiments have determined that ss-aDNA interacting with a Triton micelle should carry a hydrodynamic drag equivalent to an $\alpha$ value of $67.2 \pm 0.7$ bases. Assuming that $\mu^o{}_{aDNA} = -2.95 \times 10$ cm$^2$/Vs, this predicts that the lowest possible effective mobility (equivalent to covalent attachment of a Triton micelle) for a 25 base aDNA would be $-0.8 \times 10^{-4}$ cm$^2$/Vs. Thus, additional effects are at work other than those explained by the transient attachment of a Triton micelle as a drag-tag. In the absence of an alkylation, DNA sequencing fragments are expected to have a net electrophoretic mobility of 0. In FIG. 16(B), the electropherogram for the non-alkylated DNA primer, the lowest measurable effective mobility of the fDNA is approximately $-1.15 \times 10^{-4}$ cm$^2$/Vs. This could only result from one of two probable scenarios. First, the fixed polarity of the instrument, cathode to anode, requires that the separation be conducted under conditions of suppressed EOF. In order to suppress EOF, a small percentage (0.1% w/v) of POP6 polymer is added to the surfactant running buffer. This practice is well established in the literature and it has been observed that the presence of the polymer at such a low concentration does not induce sieving effects in free solution. It is possible, however, that the interaction of the polymer with the Triton micelles induces some strange structure that leads to increased degrees of hydrodynamic friction. It is also possible that the fluorophore itself is interacting with the micellular phase favorably resulting in a decreased electrophoretic mobility.

Comparison of FIG. 14(B) with the other three channels from the same separation indicate a strong dependence of the effective electrophoretic mobilities of the migrating fragments on the fluorophore identity, even in the absence of the aliphatic group. This strong dependence of fluorophore identity on the migrational behavior of the fDNA is expected to be present for the aDNA as well. As a consequence, each of the four channels was normalized to remove any dependence on fluorophore identity. Through comparison with the known sequence of the M13mp18 template, the migration time and hence electrophoretic mobility at the peak maximum of each fragment that passes by the detector was determined. The resulting plot of effective mobility vs. expected DNA length can be seen in FIG. 15. The dependence of the fluorophore mobility is clear since each of the fits has a different slope. While a linear fits seemed to provide the best fit over this particular range of DNA fragment lengths, a linear dependence is not expected from the ELFSE equation $$\mu_{eff} = \mu_{fDNA} \frac{L_{DNA}}{L_{DNA} + \alpha}.$$

The effective mobility of each fragment should scale hyperbolically with $L_{DNA}$ rather than the observed linear slope. This is further evidence that the physical mechanism responsible for the separation is not in fact consistent with the transient attachment of a Triton X-100 micelle to an alkylated DNA. The process is assuredly mediated by the presence of the aliphatic group with the micelle, but separation does not take place based solely through drag-tag induced increases in the tag's hydrodynamic radius. However, there still is a sufficient degree of resolution between the various fragments so a rudimentary sequence analysis should still provide adequate sequence information. To accomplish this, each of the electropherograms should be aligned such that the impact of the fluorophore is taken into account. This can be accomplished by converting the x-axis in FIG. 15 from electrophoretic mobility to length. The result of this transformation can be found in FIG. 16. This represents a region of the set of electropherograms normalized to remove fluorophore impact on the effective mobilities of the individual fragments. The sequence of this 30 base region of the M13mp18 template was determined manually. The bases can be found along the top of the figure and they match the expected sequence exactly. Although the exact mechanism for the linear relationship between electrophoretic mobility and fragment length is not firmly understood, it is most likely induced by either the presence of the EOF-suppressing polymer or the non-zero partitioning of the BigDye fluorophores to the surfactant micelles.

Thus, it was also demonstrated that the use of a large, transiently-attached drag-tag could enable ELFSE methods to compete with existing capillary gel electrophoresis-based technologies. The alkylation of the sequencing primer has no detectable impact on the fidelity of the sequencing reaction. The normalization of the electrophoretic mobility into length permitted the successful determination of the DNA fragment's sequence over a 30-base range.

Hypothetical Example 1

The lipophilic moiety can be bonded at many positions on a nucleic acid or nucleoside. For example, one could incorporate amine-containing nucleosides into the primer, or enzymatically incorporate amine-containing nucleosides into the cycle-sequencing products or PCR products. Such schemes could include nucleosides such as amino-allyl dUTP, aha-dCTP, aminohexyl-dCTP, and amino-butyl-aATP. Additionally, one could use hydrophobically modified fluorophores attached to the 3' end. Such fluorophores may be linked to ddNTP chain terminators and may contain alkyl groups. Those alkyl groups can have a hydrophilic spacer to minimize the impact of micelle binding on fluorescence signal. Such spacers may be composed of ethylene glycol subunits.

One of ordinary skill in the art would recognize other methods of linking a lipophilic moiety to the nucleic acids.

Hypothetical Example 2

Proteins can also be separated by molecular weight by transiently interacting a drag-tag with a protein-detergent complex during a separation modality. In contrast to the example using nucleic acids, the lipophilic moiety is not covalently bonded to the protein. Instead, an ionic bond binds the protein and lipophilic moiety. For example, a sample protein may be treated with a detergent such as sodium dodecyl sulfate (SDS). The SDS encases at least a portion of the protein, thereby forming a protein-detergent complex where the protein is coated with the SDS. The protein-detergent complex can then be placed in an electrophoresis device. The electrophoresis device has a running buffer. The running buffer can comprise 1 mM Triton X-100 in 50 mM Tris-MES at pH 8.0, and the electric field used can be 300 V/cm. Transient interactions of the Triton X-100 drag-tags in the running buffer with the SDS-protein complexes may lead to shifts in electrophoretic mobility that are molecular weight dependent. A similar experiment can be performed using Triton X-100-stabilized carbon nanotubes at 0.1 weight % as drag-tags in a 50 mM Tris-MES buffer at pH 8.0.

Hypothetical Example 3

In some embodiments, the invention is a method of measuring a hydrodynamic radius of a drag-tag. For example, Triton X-100-stabilized carbon nanotubes could be dispersed at 0.1 wt % in a buffer containing 50 mM Tris-HCl at pH 8.0. This buffer could be used as the running buffer as described above. A sample of alkylated DNA containing a single component of known molecular weight (number of bases) could be electrophoretically separated in the above carbon nanotube running buffer. Electrophoretic separation of the alkylated DNA in the presence of the carbon nanotube drag-tags should yield one distinct peak whose elution time (or velocity in a given electric field) reveals the hydrodynamic radius of the carbon nanotube drag-tags. The above assumes that a large number of transient interactions between the alkylated DNA and the surfactant-stabilized carbon nanotubes occur so that polydispersity in the carbon nanotube drag-tags is not evident.

Another embodiment of the invention is a method of separating drag-tags having different hydrodynamic radiuses. This embodiment comprises using a molecule, such as an alkylated DNA, that binds tightly to the carbon nanotubes, so that dynamic exchange does not occur. In this case, the polydispersity of the carbon nanotube population would be revealed by the presence of multiple peaks in the presence of the single alkylated DNA population with highly uniform molecular weight. Fractionation of the peaks could be used to separate carbon nanotubes based on their hydrodynamic radius. Other colloidal particles could be characterized and/or separated by a similar scheme, including liposomes, micelles, proteins, biomolecules, viruses, single-walled carbon nanotubes, multi-walled carbon nanotubes, oil-in-water emulsions, and solid particles coated with a surfactant.

The specific embodiments disclosed herein are not considered to be limiting. One of ordinary skill in the art would appreciate that alternative molecules, drag-tags and/or colloid particles could be used, and that the invention has alternate utilities.

Such an artisan would recognize that the invention, which generally relates to transiently binding a drag-tag to a molecule that is being separated, can function with other molecules, drag-tags, and lipophilic moieties. It is to be understood that the invention may assume alternative variations and step sequences, except where expressly specified to the contrary. It is also to be understood that the specific embodiments described in the following specification are exemplary of the invention.

The present invention is not limited to using nucleic acid analogs or protein-detergent complexes. One of ordinary skill in the art would recognize that any molecule that can be separated by various modalities could be used, so long as the molecule can move at a different rate than the drag-tag during the separation modality, and can transiently interact with at least a portion of the molecule with the drag-tag during the separation modality. Along these lines, although Triton X-100 was specifically discussed, one skilled in the art would recognize that other non-ionic surfactants could be used in the formation of the drag-tag. Additionally, cationic, anionic or zwitterionic could likewise be used, provided that the drag-tag's mobility was different from the molecule's mobility.

The invention claimed is:

1. A method of transiently attaching a drag-tag to a nucleic acid, comprising:
   a. elongating a nucleic acid primer on a nucleic acid template, the primer comprising a lipophilic moiety covalently attached to a nucleic acid, thereby forming a hydrophobically-labeled nucleic acid; and
   b. moving the hydrophobically-labeled nucleic acid through a running buffer comprising a drag-tag, wherein the drag-tag comprises a structure, and wherein the structure comprises a surfactant, a polymer or a combination thereof, wherein the lipophilic moiety is an alkyl group.

2. The method according to claim 1, wherein the alkyl group is selected from the group consisting of an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, a docosyl group, a tricosyl group and a tetracosyl group.

3. The method according to claim 1, wherein each lipophilic moiety comprises an approximately equal number of carbon atoms.

4. The method according to claim 1, wherein the structure comprises a surfactant selected from the group consisting of acetylenic glycols, alkanolamides, alkanolamines, alkyl β-D-glycopyranosides, alkyl phenols, alkylglucosides, alkylmonoglucosides, fatty acids, fatty alcohols, fatty esters, glycerol esters, monododecyl ethers, phenol derivatives, poloxamers, poloxamines, polyoxyethylene acyl ethers, polyoxyethyleneglycol dodecyl ethers, sorbitols and sorbitan derivatives, alkylphenol ethylene oxide condensates, alkyl ethylene oxide condensates, octylphenol ethylene oxide condensates, fluoroalkylphenol ethylene oxide condensates, fluoroalkyl ethylene oxide condensates, partially fluorinated fluoroalkylphenol ethylene oxide condensates, partially fluorinated fluoroalkyl ethylene oxide condensates, fluorinated hydrocarbons, partially fluorinated hydrocarbons, fluorocarbon-based surfactants, alkylamines, quaternary amines, imidazolines, dialkylamine oxides, gemini surfactants, salts of multiple acids, salts of fatty acids, sodium dodecyl sulfates, bile acid salts, isethionates, salts of tall oil acids, alcohol phosphates, inorganic phosphates, sarcosine derivatives, alcohol sulfates, alkyl phenol sulfates, sulfated triglycerides, alpha-olefin sulfonates, linear alkylbenzene sulfonates, aromatic sulfonates, sodium alkyl sulfonates, sulfosuccinates, taurates, gemini surfactants, amino acids, betaines, imidazolines, imino acids, phospholipids, gemini surfactants, and combinations thereof.

5. The method according to claim 1, wherein the structure comprises a surfactant, and wherein the surfactant is a non-ionic surfactant.

6. The method according to claim 5, wherein the non-ionic surfactant is selected from the group consisting of acetylenic glycols, alkanolamides, alkanolamines, alkyl β-D-glycopyranosides, alkyl phenols, alkylglucosides, alkylmonoglucosides, fatty acids, fatty alcohols, fatty esters, glycerol esters, monododecyl ethers, phenol derivatives, poloxamers, poloxamines, polyoxyethylene acyl ethers, polyoxyethyleneglycol dodecyl ethers, sorbitols and sorbitan derivatives, alkylphenol ethylene oxide condensates, alkyl ethylene oxide condensates, octylphenol ethylene oxide condensates, fluoroalkylphenol ethylene oxide condensates, fluoroalkyl ethylene oxide condensates, partially fluorinated fluoroalkylphenol ethylene oxide condensates, partially fluorinated fluoroalkyl ethylene oxide condensates, fluorinated hydrocarbons, partially fluorinated hydrocarbons, fluorocarbon-based surfactants, and combinations thereof.

7. The method according to claim 1, wherein the structure is selected from the group consisting of a liposome, a micelle, a solid particle, a carbon nanotube, and an oil-in-water emulsion.

8. The method according to claim 1 further comprising:
   c. applying an electric field to the running buffer for a period of time;
   d. forming a lipophilic interaction between the lipophilic moiety and the drag-tag for a portion of the period of time;
   e. terminating the lipophilic interaction formed during step (d) during the period of time;
   f. repeating steps (c) and (d) throughout at least a portion of the period of time; and
   g. discontinuing the electric field.

9. The method according to claim 1, wherein the lipophilic moiety comprises a functional group.

10. The method according to claim 9, wherein the functional group is a chromophore.

11. The method according to claim 9, wherein the functional group is a fluorophore.

12. The method according to claim 9, wherein the functional group is bodipy or a fatty acid derivative thereof.

13. The method according to claim 9, wherein the functional group is a radioactive atom.

14. The method of claim 1, in which the nucleic acid is elongated in the presence of a DNA chain terminator.

15. The method of claim 14, in which the DNA chain terminator is an acyclic nucleoside triphosphate.

16. The method of claim 14, in which the DNA chain terminator is a dideoxy nucleoside triphosphate.

17. The method of claim 16, in which the dideoxy nucleoside triphosphate is fluorescently labeled.

18. A method of separating nucleic acids:
   a. elongating a nucleic acid primer on a nucleic acid template, the primer comprising a lipophilic moiety covalently attached to a nucleic acid, thereby forming a plurality of hydrophobically-labeled nucleic acids, wherein the lipophilic moiety is an alkyl group;
   b. placing the plurality of hydrophobically-labeled nucleic acids in a running buffer comprising a drag-tag, wherein the drag-tag comprises a structure, and wherein the structure comprises a surfactant, a polymer or combinations thereof;
   c. applying an electric field to the running buffer for a period of time;
   d. forming a lipophilic interaction between the lipophilic moiety and the drag-tag for a portion of the period of time;
   e. terminating the lipophilic interaction formed during step (c) during the period of time;
   f. repeating steps (c) and (d) throughout at least a portion of the period of time; and
   g. discontinuing the electric field.

* * * * *